(12) United States Patent
Wollbold et al.

(10) Patent No.: US 9,789,262 B2
(45) Date of Patent: Oct. 17, 2017

(54) SHEATH PROTECTING A CANNULA, AND SAFETY SYRINGE COMPRISING SAID SHEATH

(71) Applicants: Jurgen Wollbold, Labruguiere (FR); Christophe Combes, Mazamet (FR); Gregory Lambert, Chatenay-Malabry (FR); Jerome Haas, Montgeron (FR); Cecile Arnaud, Paris (FR)

(72) Inventors: Jurgen Wollbold, Labruguiere (FR); Christophe Combes, Mazamet (FR); Gregory Lambert, Chatenay-Malabry (FR); Jerome Haas, Montgeron (FR); Cecile Arnaud, Paris (FR)

(73) Assignee: SOFIC (STE FRANCAISE D'INSTRUMENTS DE CHIRURGIE), Mazamet (FR)

( * ) Notice: Subject to any disclaimer, the term of this patent is extended or adjusted under 35 U.S.C. 154(b) by 55 days.

(21) Appl. No.: 14/398,256

(22) PCT Filed: May 3, 2013

(86) PCT No.: PCT/EP2013/059310
§ 371 (c)(1),
(2) Date: Oct. 31, 2014

(87) PCT Pub. No.: WO2013/164475
PCT Pub. Date: Nov. 7, 2013

(65) Prior Publication Data
US 2015/0119813 A1  Apr. 30, 2015

(30) Foreign Application Priority Data
May 3, 2012 (WO) .................. PCT/EP2012/058160

(51) Int. Cl.
*A61M 5/32* (2006.01)

(52) U.S. Cl.
CPC ........ *A61M 5/3257* (2013.01); *A61M 5/3269* (2013.01); *A61M 5/3271* (2013.01); *A61M 5/3272* (2013.01)

(58) Field of Classification Search
CPC .............. A61M 5/3257; A61M 5/3269; A61M 5/3271; A61M 5/3272; A61M 5/3202;
(Continued)

(56) References Cited

U.S. PATENT DOCUMENTS 4,834,717 A * 5/1989 Haber ................. A61M 5/24
604/193
4,994,045 A  2/1991 Ranford
(Continued)

FOREIGN PATENT DOCUMENTS

EP  1 603 612 B1  10/2009
EP  2 324 875 A1  5/2011
(Continued)

OTHER PUBLICATIONS

International Search Report, dated Jun. 19, 2013, from corresponding PCT application.

*Primary Examiner* — Quynh-Nhu H Vu
(74) *Attorney, Agent, or Firm* — Young & Thompson

(57) ABSTRACT

A protective sheath (100) for a cannula (210) arranged on a hub (200) which can be fitted onto a syringe (300), the sheath including female elements intended to cooperate with male elements (201) of the hub (200) for guiding thereof, and characterized in that the female elements include a retracted position before use RBU, a retracted position during use RU, and a retracted position after use RAU, wherein the whole length of the cannula (210) is inside the sheath (100), the female elements further include an ejection position E, wherein whole or part of the cannula (210) protrudes out of the sheath (100), and further characterized
(Continued)

in that at least two of the RBU, RU, and RAU positions are substantially transversally aligned.

21 Claims, 18 Drawing Sheets

(58) Field of Classification Search
CPC .............. A61M 5/3204; A61M 5/3205; A61M 2005/3206; A61M 5/321; A61M 5/322
See application file for complete search history.

(56) References Cited

U.S. PATENT DOCUMENTS

| | | | |
|---|---|---|---|
| 5,135,455 A * | 8/1992 | King | A63B 21/0726 482/105 |
| 5,232,457 A * | 8/1993 | Grim | A61M 5/24 604/195 |
| 5,312,370 A | 5/1994 | Talonn et al. | |
| 5,405,326 A * | 4/1995 | Haber | A61M 5/345 604/110 |
| 6,669,671 B1 | 12/2003 | Mohammad | |
| 8,128,594 B1 | 3/2012 | Chang | |
| 2003/0141210 A1 * | 7/2003 | Yanke | A61J 1/00 206/364 |
| 2004/0181247 A1 * | 9/2004 | Kehr | A61B 17/3213 606/167 |
| 2005/0171486 A1 * | 8/2005 | Hochman | A61M 5/00 604/218 |
| 2006/0184113 A1 * | 8/2006 | Jouvin | A61M 5/3272 604/110 |
| 2011/0082428 A1 * | 4/2011 | Huang | A61M 5/3272 604/198 |
| 2011/0118667 A1 * | 5/2011 | Zaiken | A61M 5/3202 604/138 |
| 2011/0319832 A1 * | 12/2011 | Chun | A61M 5/326 604/198 |
| 2012/0289905 A1 * | 11/2012 | Julian | A61M 5/20 604/189 |
| 2013/0331794 A1 * | 12/2013 | Ekman | A61M 5/326 604/197 |

FOREIGN PATENT DOCUMENTS

FR           2 852 250 A1    9/2004
WO           2006/105006 A2  10/2006

* cited by examiner

ROTATION

Tip of cannula is protected

SHEATH PROTECTING A CANNULA, AND SAFETY SYRINGE COMPRISING SAID SHEATH

FIELD OF INVENTION

The present invention relates to a sheath protecting a cannula, said sheath being primarily designed to prevent or minimize accidental needlestick injuries. The present invention also relates to a safety syringe comprising said sheath, and more particularly to a safety syringe adapted to receive a medication-containing cartridge and comprising said sheath.

BACKGROUND OF INVENTION

Needlestick injuries frequently occur among healthcare workers, introducing high risk of blood-borne pathogen infection for surgeons, assistants, and nurses, such as HIV, hepatitis B, hepatitis C or viral hemorrhagic fevers. In a UK report, 37% of nurses reported that they have sustained a needle-stick injury at some stage during their career (Prevention CfDCa, Overview: Risks and Prevention of Sharps Injuries in Healthcare Personnel, CDC, Atlanta, Ga., USA, 2004). These results have further to be read taking into account that not all needle-stick injuries are reported, and that the rate of detection may be low. In a study investigating the use of blunt needles during obstetrical laceration repair surgeries (Wilson et al., "The use of blunt needles does not reduce glove perforations during obstetrical laceration repair", Am J Obstet Gynecol., 2008, 199(6):641.e1-3), only 11% of glove perforations were detected by the physician in a study.

Strategies are available in response to these issues, including education of healthcare workers on the risks and precautions, reduction of invasive procedures, management of exposures and use of safer devices.

Among the safest devices, an efficient way to protect a healthcare worker from being pricked by a needle is the use of safety syringes. Such syringes have the particularity to comprise a sheath protecting the needle, which can be retracted or extended. In a retracted position, the needle is completely covered and secured by the sheath. In an extended position, the needle projects outside the sheath.

A major issue when designing such safety syringes, further to securing the needle, is the ease of use of said safety syringes. Even though the protection sheath may enhance safety, its volume may make the syringe uneasy and cumbersome to manipulate.

Several safety syringes comprising a sheath have been proposed in the literature. However, none of them describes a sheath according to the invention, designed for an improved convenience and an improved safety for the healthcare worker.

For example, International Patent application WO 2006/105006 discloses a safety syringe including locking positions, formed by an inner sleeve receiving a cartridge filled with liquid, an outer sleeve through which said inner sleeve is telescopically reciprocated, and a plunger assembly that is attached to the inner sleeve and used to eject the liquid. This device is capable of both intermittent locking during use RU as well as permanent locking after use RAU (page 5, lines 2-3), performed by pushing inward a tab which engages permanently a hole. However, there is no specific retracted position before use RBU.

US patent 2011/0082428 relates to a safety structure for covering a syringe needle including a safety sleeve and a hub. The safety sleeve is fitted around the hub and provided with an axial sliding slot, a locating slot laterally extended from the sliding slot and a locating hole located at a bottom of the locating slot. The protective sheath comprises a "retracted position before use" in the locating slot, an "ejection position" in the sliding slot and a "retracted position after use" in the locating hole. However, this device does not provide a "retracted position during use". Moreover, this safety structure does not provide a one-way path for the male means of the hub through the female means of the safety sleeve: backtracks are indeed needed in order to access to the various retracted positions (RBU, RU and RAU). Thus said safety structure lacks of convenience and safety.

U.S. Pat. No. 4,994,045 discloses a safety syringe including a conventional syringe, a locating ring and an elongated and tubular sheath. This device is capable of both intermittent and permanent positions where the needle is secured, allowing the user to extend or retract the tubular sheath at will during use (ejection position E and retracted position during use RU), and to definitely secure the needle after use (retracted position after use RAU). However, the various retracted positions are not transversally aligned (see FIG. 2 of U.S. Pat. No. 4,994,045), resulting in a non-optimized sheath length as described further in the description of the invention.

European Patent EP 1 603 612 discloses a preservative sheath for an injection needle or cannula arranged on a cannula-holding support which can be fitted onto a syringe. The sheath comprises guide means, which may be ramps, allowing the cannula to be in a retracted position before use RBU, a retracted position during use RU, a retracted position after use RAU and an ejection position E. However, the various retracted positions are not transversally aligned, resulting in a non-optimized sheath length as described further in the description of the invention. Moreover, the RU position comprises no temporary locking means.

U.S. Pat. No. 5,312,370 discloses a needle protecting device adapted for use on a standard syringe, especially a conventional dental syringe able to receive a cartridge. The sheath of this device may be rotated from an intermediate locked position during use RU to a final locked position after use RAU securing the needle. However, there is only one possible intermediate locked position (as described column 8 of U.S. Pat. No. 5,312,370). This device provides no specific retracted position before use RBU.

Therefore, there is still a need in the art for a needle protective sheath improving the healthcare worker's convenience and safety.

SUMMARY

A first object of the present invention is a protective sheath for a cannula arranged on a hub which can be fitted onto a syringe, said sheath comprising female means intended to cooperate with male means of the hub for guiding thereof, and characterized in that:
  said female means comprise a retracted position before use RBU, a retracted position during use RU, and a retracted position after use RAU, wherein the whole length of the cannula is inside said sheath;
  said female means comprise an ejection position E, wherein whole or part of the cannula protrudes out of said sheath; and
  at least two of the RBU, RU, and RAU positions are substantially transversally aligned.

Female means of the sheath according to the invention may include:
- primary transition means for insertion of male means of the hub within the sheath and for guiding said male means to the RBU position;
- primary locking means for temporary locking said male means in the RBU position;
- secondary transition means for guiding said male means from the RBU to the RU position;
- secondary locking means for temporary locking said male means in the RU position;
- guiding means, for guiding said male means forth from the RU position to the E position and back from the E position to the RU position;
- tertiary transition means for guiding said male means from the RU position to the RAU position; and/or
- final locking means, for permanently locking said male means in the RAU position.

In one embodiment, said male means are bosses. In one embodiment, female means are in the form of holes and/or grooves in the internal surface of the sheath.

Primary transition means may preferably be one-way transition means comprising anti-return means.

Secondary transition means may advantageously include translation/rotation guiding means from the RBU position to a transitory position T, and longitudinal guiding means from the T position to the RU position, said longitudinal guiding means being preferably one-way transition means comprising anti-return means.

In one embodiment, tertiary transition means may include rotational guiding means.

The sheath may further comprise anti-slipping means. For example, said anti-slipping means include inclined planes and/or at least one rib.

Anti-slipping means may further include means for preventing dismounting of the hub from the sheath, such as for example at least one rib.

The distal end of the sheath according to the invention may preferably be conical or beveled.

The sheath may further comprise gripping means, which are preferably ribs covered by a grinding or an erosion grain such as VDI 20 to 30, located on the external surface of the sheath.

Thus, the sheath according to the invention may comprise 1, 2, 3, 4 or all of the following features:
- female means are in the form of holes and/or grooves in the internal surface of said sheath cooperating with male means which may be bosses;
- said sheath comprises anti-slipping means, including:
  - inclined planes and/or at least one rib; and/or
  - at least one rib for preventing dismounting of the hub from said sheath;
- at least one end of said sheath is conical;
- said sheath comprises gripping means which are ribs covered by a grinding or an erosion grain such as VDI 20 to 30, located on the external surface of the sheath.

A second object of the present invention is a hub adapted to be inserted within a sheath as described above, comprising:
- male means, adapted to cooperate with female means of the sheath wherein the hub may be inserted; and
- optionally a cannula, protruding at both ends of the hub.

In an embodiment, the hub comprises reception means located at one end of the hub and designed to receive a syringe.

A third object of the present invention is an injection system, comprising a sheath as described above and a hub cooperating with said sheath, as described above. In one embodiment, the hub is inside the sheath.

A fourth object of the present invention is a syringe including a sheath or an injection system as described above.

The syringe of the invention may be a standard syringe comprising a plunger, a barrel or a carpule-holder and means for being adapted on a hub of the invention or an injection system of the invention. In an embodiment, the syringe is adapted for dentistry.

In an embodiment, the syringe of the invention is designed to hold a cartridge; preferably the cartridge is immobilized in radial direction via demolding clips and the back of the syringe, and/or in axial direction at the neck of said cartridge via a clip which is preferably flexible.

The plunger of a syringe according to the invention may be advantageously equipped with a plunger seal comprising lips, wherein said lips may bend backwards for an easier introduction into the cartridge. According to one embodiment, the plunger seal is overmolded on the plunger.

The syringe may further comprise soft overmoldings installed in the thumb area and in the grip area of said syringe.

According to an embodiment, the syringe of the invention is disposable. In this embodiment, wherein the syringe is disposable, the syringe may have a precut located substantially at the distal end of the syringe, being for example a series of perforations or one or more circumferential grooves, preferably one circumferential groove.

According to an embodiment, the cartridge of said syringe is immobilized in radial direction via demolding clips and the back of the syringe; and the plunger of said syringe is equipped with a plunger seal comprising lips, wherein said lips may bend backwards for an easier introduction into the cartridge, said plunger seal being optionally overmolded on the plunger.

Thus, the syringe according to the invention may comprise 1, 2, 3 or all of the following features:
- the cartridge is immobilized in radial direction via demolding clips and the back of the syringe;
- the plunger of said syringe is equipped with a plunger seal comprising lips, wherein said lips may bend backwards for an easier introduction into the cartridge, said plunger seal being optionally overmolded on the plunger;
- said syringe comprises soft overmoldings installed in the thumb area and in the grip area of said syringe;
- said syringe has a precut located substantially at the distal end of the syringe, made of a series of perforations or one or more circumferential grooves, preferably one circumferential groove.

A fifth object of the present invention is a syringe designed to hold a cartridge, wherein the cartridge may be immobilized in radial direction via demolding clips and the back of the syringe, and/or in axial direction at the neck of said cartridge via a clip which is preferably flexible. In an embodiment, this syringe comprises a sheath of the invention, a hub of the invention or an injection system of the invention.

A sixth object of the present invention is a manufacturing device, preferably a mould or an assembly machine, for manufacturing a hub, a sheath, and/or a syringe according to the invention.

DEFINITIONS

In the present invention, the following terms have the following meanings:

"About" preceding a value means plus or less 10% said value.

An "anti-return" means is here a means allowing the passage of a male means within a female means from a first position to a second position, and preventing the passage from the second position to the first position.

"Cannula" refers to a tube that can be inserted into the body, generally for the delivery or removal of a fluid.

"Cartridge" refers generally to a small sealed vial, used to contain and/or preserve a pharmaceutical composition.

The hub is "definitely locked" within the sheath if said hub may move with regard to said sheath only if a brutal external force is applied, for example a force able to break the device.

"Distal end" of a part refers to the farthest end of this part, relative to a point of origin. Most often the point of origin is the user and the distal end is the closest end to the tissue area in which the medicine will be injected.

"Distinct" means physically separate. "Distinct positions" refer thus to physically or materially separate position.

"Ejection position" refers here to a position of the hub when the cannula protrudes the sheath at least partially, rendering possible to insert the cannula in a patient for an injection for example.

"Female means" refers to any cavity or hole in any shape, such as a groove, at the surface or through a material, cooperating with a male means. In other words, male means may be inserted into female means and may move inside.

"Hub" refers to a piece capable of connecting a cannula to the distal end of a syringe according to the invention, or more generally to the distal end of any syringe, wherein the distal end of a syringe is the end farthest to the piston.

The verb "guiding" used with male and female means, means that said female means provide a path via hole or grooves for instance, in which said male means may move freely, and prevent said male means to step out of said path, via walls or inclined planes for instance.

"Insertion" of the male means refers here to the insertion of said male means within the female means of the sheath, said female means being possibly designed as to facilitate the insertion of said male means. For example, female means may be provided with a special opening in which male means are easily inserted. Insertion means may be also provided with an anti-return means, so that once inserted, male means cannot be removed from the female means.

"Integrally formed" refers to a part in one piece, or to a part comprising several components, wherein any components making up the part have been rendered securely jointed.

A "locking means" refers here to a part which prevents male means to step out of a defined position.

"Male means" refers to any part constituted by matter, cooperating with female means. In other words male means may be inserted into female means and may move inside.

A "Position" refers to a specific location within the female means of the sheath, wherein the male means are immobilized by for example sheath walls, locking means and/or transition means.

"Pharmaceutical composition" refers to a composition comprising an active principle in association with a pharmaceutically acceptable vehicle or excipient. A pharmaceutical composition is for therapeutic use, and relates to health. Especially, a pharmaceutical composition may be indicated for treating or preventing a disease. According to the invention, the term "treating a disease" refers to reducing or alleviating at least one adverse effect or symptom of a disease, disorder or condition associated with a deficiency in an organ, tissue or cell function. The expression "Preventing a disease" or "Inhibiting the development of a disease" refers to preventing or avoiding the occurrence of symptom.

"Priming position" refers to a position in which the user releases the air from the syringe and depresses the plunger until a small amount of the liquid medium comes out.

"Protective sheath" or "sheath" refers here to a removable element preventing an easy access to another element able to hurt. It may be for example a tube preventing fingers to access a needle, which may be retracted or extended.

"Proximal end" of a part refers to the closest end of this part, relative to a point of origin. Most often the point of origin is the user and the proximal end is the farthest end from the tissue area in which the medicine will be injected.

"Retracted position" refers here to a position of the hub when the cannula is protected within the sheath, preventing fingers for example to access said cannula.

"Rotational movement" refers here to the rotation of the hub within the sheath, around the axis of the cylinder.

"Standard syringe" refers to a syringe comprising a barrel, wherein an injectable composition may be directly loaded.

"Substantially" at the end of a part means that the location ranges from 0.01 to 25% of the total length of said part from said end.

"Syringe" refers to any device comprising a container or a means intended to receive a container, an opening and a piston, wherein said piston is used to push the content of said container through said opening.

The hub is here "temporary locked" within the sheath if the movement of said hub with regard to said sheath cannot spontaneously occur under common natural forces such as gravity, but requires an external force.

"Transition means" refers to a path within the sheath allowing male means to step from a first position to a second position. A transition means may comprise an anti-return means so that said male means, once in the second position, cannot move back to the first position anymore.

"Translation movement" refers here to a longitudinal movement, having the same direction than the axis of the cylinder.

"Transversally aligned" refers here to the property of various points on a tube having a longitudinal axis X, wherein each point has the same coordinate along the X axis. "Substantially transversally aligned" refers here to the property of various points on a tube having a longitudinal axis X, wherein each point has the same coordinate plus or minus 3 mm, preferably plus or minus 2.5 mm, more preferably plus or minus 1.5 mm, even more preferably plus or minus 0.5 mm, still more preferably plus or minus 0.25 mm along the X axis.

| LIST OF REFERENCES | |
|---|---|
| 100 | Sheath |
| 101 | Gripping means |
| 102 | Distal end of the sheath |
| 103 | Proximal end of the sheath |
| 104 | Internal surface of the sheath |
| 105 | External surface of the sheath |
| 106 | Rib |
| 107 | Rib |
| 110 | Primary transition means |
| 111 | Hole |
| 120 | Primary locking means |
| 121 | Inclined plane |
| 130 | Secondary transition means |
| 131 | Translation/rotation guiding means |
| 132 | Longitudinal guiding means |
| 133 | Inclined plane |
| 134 | Hole |
| 135 | Hole |
| 140 | Secondary locking means |
| 150 | Guiding means |
| 151 | Inclined plane |
| 152 | Guiding means (second part) |
| 160 | Tertiary transition means |
| 170 | Final locking means |
| 171 | Inclined plane |
| 172 | Inclined plane |
| 200 | Hub |
| 201 | Bosses |
| 202 | Distal end of the hub |
| 203 | Proximal end of the hub |
| 204 | Reception means of the hub |
| 205 | Bottom of the reception means |
| 206 | Internal diameter of the hub |
| 207 | External diameter of male means |
| 208 | Inclined plane |
| 209 | Gap |
| 210 | Cannula |
| 211 | Proximal end of the cannula |
| 300 | Syringe |
| 301 | Embossment |
| 302 | Grip area |
| 303 | Self demolding clip |
| 304 | Back of the syringe |
| 305 | Blocking means |
| 306 | Precut |
| 310 | Plunger |
| 311 | Thumb area |
| 312 | Plunger seal |
| 313 | Lips |
| 400 | Cartridge |
| 401 | Rear piston of the cartridge |
| 402 | Neck of the cartridge |

DETAILED DESCRIPTION

Protective Sheath

The present invention relates to a protective sheath 100 for a cannula 210 arranged on a hub 200 which can be fitted onto a syringe 300, allowing a safe use of said cannula 210 without the risk of being accidentally pricked.

Figure 1:
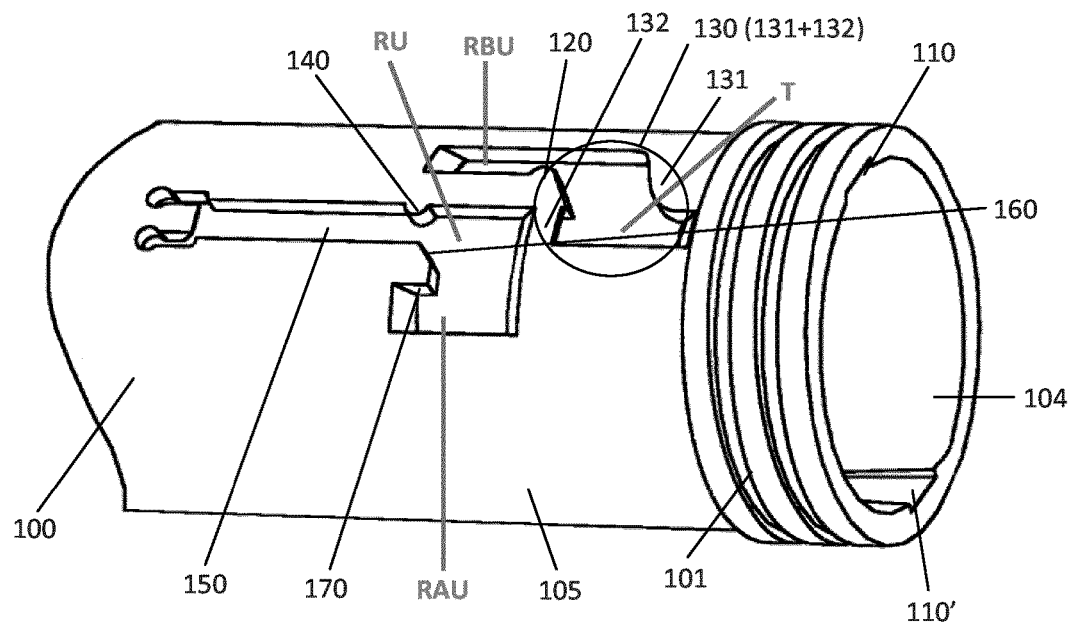
FIG. 1 is a perspective view showing a portion of a sheath according to the invention, comprising locking, guiding and transition means.

As shown in FIG. 1, the sheath 100 has an overall shape of a hollow cylinder having a longitudinal axis X. In an embodiment, the sheath 100 has an internal diameter preferably ranging from 3 to 20 mm. In another embodiment, the sheath 100 has an external diameter preferably ranging from 4 to 21 mm. In one embodiment, the external and internal diameters of the sheath 100 are preferably substantially constant, at least in a first section. In one embodiment, a substantially constant diameter means that said diameter may vary of maximum 20%, preferably 10%, more preferably 5%, even more preferably 1%, from its nominal value (in other words the desired value).

In still another embodiment, the sheath 100 has a length preferably ranging from 30 to 150 mm.

In one embodiment, the sheath 100 is made of plastic, preferably transparent so that the cannula 210 may be visible through the sheath 100. In another embodiment, the sheath 100 is opaque. In one embodiment, the thickness of the sheath 100 is preferably substantially constant (for example with a variation of maximum 20%, 10%, 5%, or 1% from its nominal value), but may be narrowed at non protective locations to save matter, for example at the distal and proximal ends 102 and 103 of said sheath 100. In one embodiment, the thickness of the sheath 100 is comprised between 0.2 and 5 mm, preferably between 0.5 and 3 mm, more preferably between 1 and 2 mm, and said thickness may be narrowed of between 20 and 60% at non-protective locations.

Figure 2:
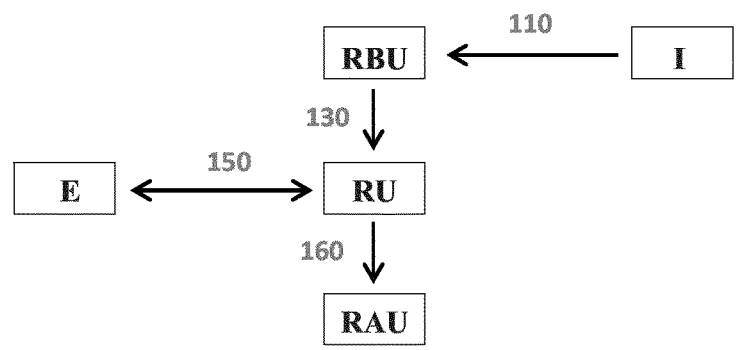
FIG. 2 is a schema showing the various positions of the hub in the sheath, according to the invention.

The sheath 100 comprises female means which comprises structure (further described hereafter) structured to cooperate with structure forming a male means, e.g. one or more bosses 201, of the hub 200, said female means allowing said hub 200 to be in various positions, as depicted in FIG. 2. In one embodiment female means cooperate with male means 201 of the hub 200, said hub 200 being movable between the following positions:

an insertion position I, wherein the hub 200 is introduced at the proximal end 103 of the sheath 100;
three retracted positions, wherein the hub 200 and the whole length of the cannula 210 are inside the sheath 100:
  a retracted position before use RBU, wherein the hub 200 and the cannula 210 are temporary locked inside the sheath 100;
  a retracted position during use RU, wherein the hub 200 and the cannula 210 are temporary locked inside the sheath 100;
  a retracted position after use RAU, wherein the hub 200 and the cannula 210 are definitely locked inside the sheath 100;
an ejection position E, wherein the hub 200 is substantially at the distal end 102 of the sheath 100, so that whole or part of the cannula 210 protrudes out of the sheath 100. This E position is reachable from the RU position only.

The various positions of the hub 200 inside the sheath 100 contribute to the healthcare worker's safety, in that:
the RBU position prevents needlestick injuries (NSIs) before use of cannula 210;
the RU position prevents NSIs during use of cannula 210;
the RAU position prevents NSIs after use of cannula 210.

In a preferred embodiment, the insertion position, the retracted position before use, the retracted position during use, the ejection position and the retracted position after use are distinct one from another.

In another embodiment, the retracted position before use, the retracted position during use and the retracted position after use are distinct one from another.

In another embodiment, the retracted position before use and the retracted position during use are distinct.

In a preferred embodiment, the sheath 100 of the present invention includes at least 3 retracted positions (RBU, RU and RAU). In a preferred embodiment, the sheath 100 of the present invention includes more than 2 retracted positions. In an embodiment, the invention does not include any device featuring two retracted positions only.

In another embodiment, the sheath 100 does not provide a priming position distinct from the ejection position.

In an embodiment, the male means 201 is not temporary locked in the ejection position.

In an embodiment, the male means 201 is temporary locked in the ejection position.

The passage of male means 201 between the various positions and the immobilization of said male means 201 within the female means of the sheath 100 are rendered possible via:

primary transition means 110, for insertion of male means 201 of the hub 200 within the sheath 100, and for guiding said male means 201 to the RBU position;
structure forming a primary locking means 120 (further described below) for temporary locking said male means 201 in the RBU position;
secondary transition means 130 for guiding said male means 201 from the RBU position to the RU position;
secondary locking means 140 for temporary locking said male means 201 in the RU position;
guiding means 150, for guiding said male means 201 forth from the RU position to the E position and back from the E position to the RU position;
tertiary transition means 160 for guiding said male means 201 from the RU position to the RAU position;
final locking means 170, for permanently locking said male means 201 in the RAU position.

Primary, secondary and tertiary transition means 110, 130 and 160 are preferably one-way transition means, meaning that they allow the transition from a first position to a second position only, but do not allow the reverse transition back from the second position to the first position. These transition means comprise therefore advantageously anti-return means. The achievement of a one-way path (i.e. without reverse transition) through the various retracted positions (RBU, RU and RAU) via the transition means (110, 130, and 160) ensures an ease of use. In one embodiment, the sheath 100 contains female means which provide a precise continuous one-way path for the male means 201; therefore avoiding routing errors and making use easier and safer. In one embodiment, the sheath 100 contains female means which provide a precise one-way path for the male means 201; therefore avoiding routing errors and making use easier and safer.

In one embodiment, the guiding means 150 is the only means which allows reverse transition. It is obvious from one skilled in the art that the guiding means 150 to the ejection position has to allow reverse transition.

The various positions, being successively reached, prevent a cannula 210 equipped with said sheath 100 to be re-used.

A major drawback of using a protective sheath on a cannula is the reduction of manipulation freedom during operation, due to the volume of said sheath.

It has been therefore a goal for the present invention to provide a sheath as short as possible in order to facilitate manipulation during operation, but long enough to ensure a safe manipulation of the device.

A safe manipulation of a cannula 210 inserted into a sheath 100 is obtained when safety lengths between the sharp edges of the cannula and the sheath ends are respected (at both distal and proximal end 102 and 103). The sheath 100 has therefore to be as long as the cannula length plus the safety lengths. Safety length depends on the diameter of the opening at the sheath end, from where a cannula end may be accessed. Typically, a safety length of between 1 and 5 mm, preferably about 3 mm, has to be respected if the diameter of the opening at the sheath end is of about 10 mm.

The present invention provides a protective sheath 100 in which the proximal and distal portions of the cannula 210 are protected. For specific applications, the cannula 210 arranged on the hub 200 has to exceed the proximal end of the hub 203. For instance in dentistry, the proximal end of the cannula 211, protruding from the proximal end of the hub 203, perforates the carpule hold in the barrel of a syringe when said syringe is inserted inside the proximal part of the sheath 103. Therefore it is necessary to protect the user from the proximal end of the cannula 211. In the present invention the RBU, RU and RAU positions are positioned such as the proximal end and the distal end of the cannula 210 are contained inside the sheath 100.

In one embodiment of the present invention, the cannula 210 may be totally contained inside the sheath 100. Especially, in the invention, the protection of the cannula 210 is granted only by the sheath 100 and not by the hub 200.

In one aspect, the present invention aims at protecting healthcare worker from needlestick injuries. In an embodiment, the sheath does not to prevent a patient from seeing the needle prior to an injection. In another embodiment, the sheath prevents a patient from seeing the needle prior to an injection.

The Applicant found that, when the various retracted positions RBU, RU and RAU are transversally aligned, wherein the three positions are in the same cross-section, the sheath length is optimized. Aligned retracted positions allow the sheath to be the shortest possible while effectively protecting the cannula.

The provision of a short sheath results in a full adaptability of the sheath on the smallest syringes on market when still using a long cannula length.

Thus, the present invention provides a sheath 100 having an optimized sheath length, wherein at least two of the RBU, RU and RAU positions, preferably all of the RBU, RU and RAU positions are substantially transversally aligned. In a preferred embodiment, the RBU, RU and RAU are substantially transversally aligned. In another embodiment, the RBU and RU are substantially transversally aligned. In another embodiment, the RU and RAU are substantially transversally aligned. In another embodiment, the RBU and RAU are substantially transversally aligned. In one embodiment, the transversal alignment is respected for the aligned positions with a tolerance of 6 mm, preferably 5 mm, more preferably 3 mm, even more preferably 1 mm, still more preferably 0.5 mm. In other words, the absolute difference between the smallest and the greatest coordinate of the different aligned positions along the X axis does not exceed the value of said tolerance.

As disclosed in FIG. 2, the female means of the sheath 100 provides a one way path for the male means 201 from the RBU position to the RAU position through the RU position. The female means of the sheath 100 also allows the male means to go from the RU position to the E position and conversely.

In one embodiment, the male means 100 moves transversally respectively from the RBU position to the RU position and then to the RAU position.

In one embodiment, the male means 100 moves transversally respectively from the I position to the RBU position, the RU position and then to the RAU position.

In one embodiment, the male means 100 moves transversally respectively from the I position to the RBU position, the RU position, the E position, the RU position and then to the RAU position.

In order to better secure the use of a cannula 210 arranged on a hub 200, the transition of male means 201 of said hub 200 from a RBU position to a RU is advantageously performed via two steps:
- a displacement of said hub 200 within the sheath 100 toward the proximal end 103 of said sheath 100;
- a displacement of said hub 200 within the sheath 100 toward the distal end 102 of said sheath 100.

The two-step transition between the RBU position to the RU position results in improved safety, where the cannula 210 arranged on the hub 200 inserted into the sheath 100 is less likely to protrude said sheath 100 hazardously.

Thus, in one embodiment, a structure for secondary transition means 130 includes translation/rotation guiding means formed as a hole 131 for guiding male means 201 from the RBU position to a transitory position T, and longitudinal guiding means formed as a groove 132 for guiding said male means 201 from the T position to the RU position.

In one embodiment, longitudinal guiding means 132 are one-way transition means comprising anti-return means.

In an embodiment, tertiary transition means 160 are actuated via a rotational movement of the hub 200 inside the sheath 100, preferably via an unscrewing movement. This feature combines the entering in the final lock position of the sheath 100 with the natural gesture of the user in cannula 210 end life management. Thus, if a syringe 300 is screwed in the hub 200, the transfer into the final locked position RAU has the advantage to be automatic when the user unscrews the syringe 300.

Thus, in one embodiment, tertiary transition means 160 include rotational guiding means.

In a preferred embodiment, the final lock position of the sheath 100 can be reached only from the RU position and not from the RBU position. In another embodiment, the male means 201 moves from the ejection position to the RAU position only through the RU position. In another embodiment, the male means 201 moves from the ejection position to the RAU position without passing through the RBU position. Moreover, the male means 201 reaches the RU position from longitudinal translation guiding means 132 and not from rotational transition means, thus avoiding routing errors as guiding means 150 (used in one of the following steps, cf. FIG. 2) comprises also a longitudinal groove in the axis of the transition means 132. In one embodiment, the guiding means 150 is in line with the longitudinal translation guiding means 132.

In an embodiment, the secondary locking means 140 is compulsory between the RU position and the ejection position E.

For the efficacy of the product, the hub 200 has to remain in the sheath 100. Unfortunately, as a result of the fabrication process, a gap 209 between the sheath 100 and the hub 200 in the locking area cannot be avoided, as described FIG. 7. Thus, a risk exists that male means 201 on the hub 200 slip under the sheath 100, which eliminates the safety feature of the device.

Therefore, for safety improvement, the sheath 100 according to the invention may further comprise anti-slipping means.

In one embodiment, anti-slipping means include inclined planes 208 at the ends of male means 201. In one embodiment, anti-slipping means include inclined planes at strategic locations 121, 133, 171 and 172 on the walls of the sheath 100, as described in FIGS. 1, 3, 4 and 5. In one embodiment, anti-slipping means include inclined planes 208 at the ends of male means 201 and at strategic locations 121, 133, 171 and 172 on the walls of the sheath 100, as described in FIGS. 1, 3, 4 and 5. The angles of the inclined planes are such that when forces are applied in an axial direction, forces perpendicular to the axis force the sheath 100 to get narrower to the hub 200. The angles range preferably from 30° to 60°, more preferably from 40° to 50°, even more preferably about 45°.

Therefore, the slipping of the hub 200 under the sheath 100 is avoided, and the safety is improved.

Figure 7:
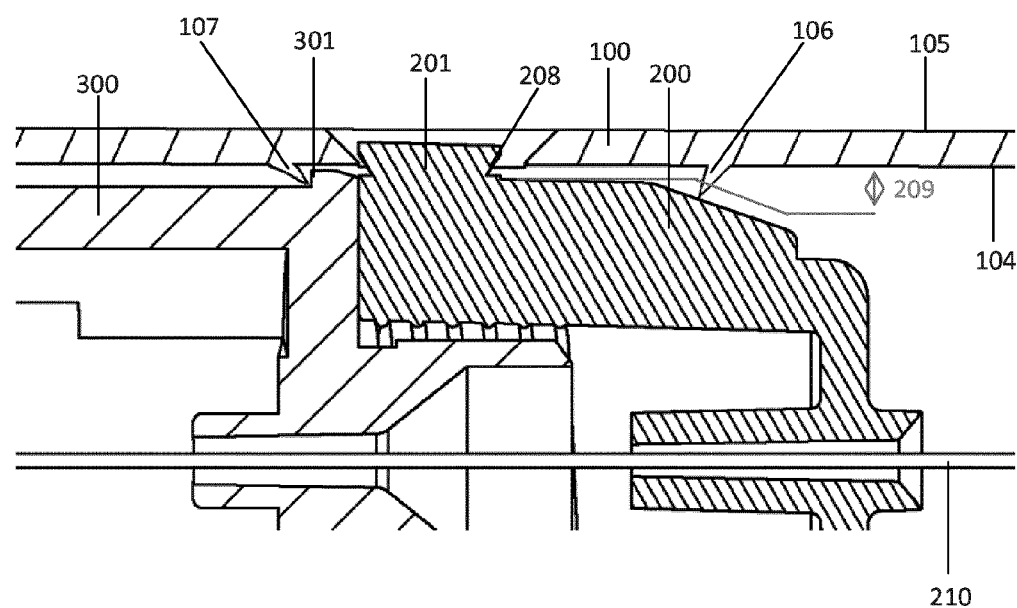
FIG. 7 is a fragmentary cross-sectional view showing a hub, a portion of a sheath and a portion of a syringe according to the invention, said syringe being screwed into the hub and said hub being inserted into the sheath, wherein the sheath further comprises anti-slipping means.

In an embodiment, anti-slipping means further include at least one rib 106, located just next to any hole or groove of the sheath 100 toward the distal end 102 of said sheath 100 so that male means 201 are not likely to pass across said rib 106 if a slipping of the hub 200 within the sheath 100 occurs (FIG. 7).

In an embodiment, anti-slipping means include means for preventing dismounting of the hub 200 from the sheath 100. Although proper use of the device is supposed, the misuse of the device has also to be taken into consideration. In this embodiment, at least one rib 107 may be added, in combination with an embossment 301 present on the hub 200 or near the distal end of the syringe 300, as depicted in FIG. 7. This rib 107 is advantageously designed so that once the hub 200 is inserted in the sheath 100 and is passed across said rib 107, this rib 107 prevents said hub 200 to step back, acting thus as a non-dismountable feature. This rib 107 may be installed near the proximal end of the sheath 100, for example in the first 4 cm, 3 cm, 2 cm or 1 cm on the internal surface 104 of said sheath 100.

Still for a safety improvement, the distal end 102 of the sheath 100 is preferably conical or beveled. This shape results on providing a large opening for a cannula 210 which may be inadvertently bended, and in being tight enough at the distal end to avoid the fingers to access said cannula 210. In one embodiment, the proximal end 103 of the sheath 100 is not conical or beveled in order to easy the insertion of the distal end of a syringe 300. In an embodiment, the protective sheath 100 has a length adapted to protect the user from needlestick.

In one embodiment, the distal end 102 of the sheath 100 does not comprise any additional piece, such as a plug, to prevent the hub 200 to step out of the sheath 100.

In one embodiment, the sheath 100 further comprises gripping means 101, providing a good grip toward the gloves of healthcare workers. Said gripping means 101 may be for example ribs, preferably covered by a grinding or an erosion grain like VDI 20 to 30.

As shown in FIGS. 1, 3, 4 and 5, all transition and locking means may be provided with holes, grooves, inclined planes and/or lugs, arranged in two identical systems diametrically opposite on the sheath 100 regarding the axis X, so that one system allows the movement and the locking of a first male means 201 of the hub 200 and the second system allows the movement and the locking of a second male means 201' of the hub 200. Said male means 201 and 201' are moved by pushing, pulling and/or rotating with one hand a syringe 300 engaged in the hub 200, and by holding the sheath 100 with the other hand.

More than two systems are possible, for example three, four, five or six systems. In all cases, all systems are preferably identical and regularly spaced along a path centered on the axis X.

In one embodiment, the sheath 100 of the present invention comprises female means which are in the form of holes and/or grooves in the internal surface 104 of said sheath 100.

In another embodiment, the sheath 100 of the present invention comprises anti-slipping means, including inclined planes 121, 133, 171, 172 and/or at least one rib 106; and/or at least one rib 107 for preventing dismounting of the hub 200 from said sheath 100.

In another embodiment, the sheath 100 of the present invention comprises:
anti-slipping means, including:
inclined planes 121, 133, 171, 172 or at least one rib 106; or
at least one rib 107 for preventing dismounting of the hub 200 from said sheath 100.

In another embodiment, the sheath 100 of the present invention comprises:
anti-slipping means, including:
inclined planes 121, 133, 171, 172 and at least one rib 106; or
at least one rib 107 for preventing dismounting of the hub 200 from said sheath 100.

In another embodiment, the sheath 100 of the present invention comprises:
anti-slipping means, including:
inclined planes 121, 133, 171, 172 and at least one rib 106, and
at least one rib 107 for preventing dismounting of the hub 200 from said sheath 100.

In another embodiment, the sheath 100 of the present invention comprises a conical or beveled distal end.

In another embodiment, the sheath 100 of the present invention comprises gripping means 101 which are ribs covered by a grinding or an erosion grain such as VDI 20 to 30, located on the external surface 105 of said sheath 100.

In another embodiment, the sheath 100 of the present invention comprises:
female means which are in the form of holes and/or grooves in the internal surface 104 of said sheath 100; and
anti-slipping means, including:
inclined planes 121, 133, 171, 172 and/or at least one rib 106; and/or
at least one rib 107 for preventing dismounting of the hub 200 from said sheath 100.

In another embodiment, the sheath 100 of the present invention comprises:
female means which are in the form of holes and/or grooves in the internal surface 104 of said sheath 100; and
a conical or beveled distal end.

In another embodiment, the sheath 100 of the present invention comprises:
female means which are in the form of holes and/or grooves in the internal surface 104 of said sheath 100; and
gripping means 101 which are ribs covered by a grinding or an erosion grain such as VDI 20 to 30, located on the external surface 105 of said sheath 100.

In another embodiment, the sheath 100 of the present invention comprises:
anti-slipping means, including:
inclined planes 121, 133, 171, 172 and/or at least one rib 106; and/or
at least one rib 107 for preventing dismounting of the hub 200 from said sheath 100; and
a conical or beveled distal end.

In another embodiment, the sheath 100 of the present invention comprises:
  anti-slipping means, including:
    inclined planes 121, 133, 171, 172 and/or at least one rib 106; and/or
    at least one rib 107 for preventing dismounting of the hub 200 from said sheath 100; and
  gripping means 101 which are ribs covered by a grinding or an erosion grain such as VDI 20 to 30, located on the external surface 105 of said sheath 100.

In another embodiment, the sheath 100 of the present invention comprises:
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including inclined planes 121, 133, 171, 172 and/or at least one rib 106; and
  a conical or beveled distal end.

In another embodiment, the sheath 100 of the present invention comprises:
  female means which are in the form of holes and/or grooves in the internal surface 104 of said sheath 100;
  anti-slipping means, including at least one rib 107 for preventing dismounting of the hub 200 from said sheath 100; and
  a conical or beveled distal end.

In another embodiment, the sheath 100 of the present invention comprises:
  female means which are in the form of holes and/or grooves in the internal surface 104 of said sheath 100;
  anti-slipping means, including:
    inclined planes 121, 133, 171, 172 and/or at least one rib 106; and
    at least one rib 107 for preventing dismounting of the hub 200 from said sheath 100; and
  a conical or beveled distal end.

In another embodiment, the sheath 100 of the present invention comprises:
  female means which are in the form of holes and/or grooves in the internal surface 104 of said sheath 100;
  anti-slipping means, including inclined planes 121, 133, 171, 172 and/or at least one rib 106; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including at least one rib 107 for preventing dismounting of the hub 200 from said sheath 100; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including:
    inclined planes 121, 133, 171, 172) and/or at least one rib 106; and
    at least one rib 107 for preventing dismounting of the hub 200 from said sheath 100; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  anti-slipping means, including at least one rib 107 for preventing dismounting of the hub 200 from said sheath 100;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  anti-slipping means, including inclined planes 121, 133, 171, 172 and/or at least one rib 106;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  anti-slipping means, including:
    inclined planes 121, 133, 171, 172 and/or at least one rib 106; and
    at least one rib 107 for preventing dismounting of the hub 200 from said sheath 100;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including inclined planes 121, 133, 171, 172 and/or at least one rib 106;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including at least one rib 107 for preventing dismounting of the hub 200 from said sheath 100;
  a conical or beveled distal end; and
  gripping means 101 which are ribs covered by a grinding or an erosion grain such as VDI 20 to 30, located on the external surface 105 of said sheath 100.

In another embodiment, the sheath 100 of the present invention comprises:
  female means which are in the form of holes and/or grooves in the internal surface 104 of said sheath 100;
  anti-slipping means, including:

inclined planes 121, 133, 171, 172 and/or at least one rib 106; and at least one rib 107 for preventing dismounting of the hub 200 from said sheath 100;

a conical or beveled distal end, and gripping means 101 which are ribs covered by a grinding or an erosion grain such as VDI 20 to 30, located on the external surface 105 of said sheath 100.

Figure 3:
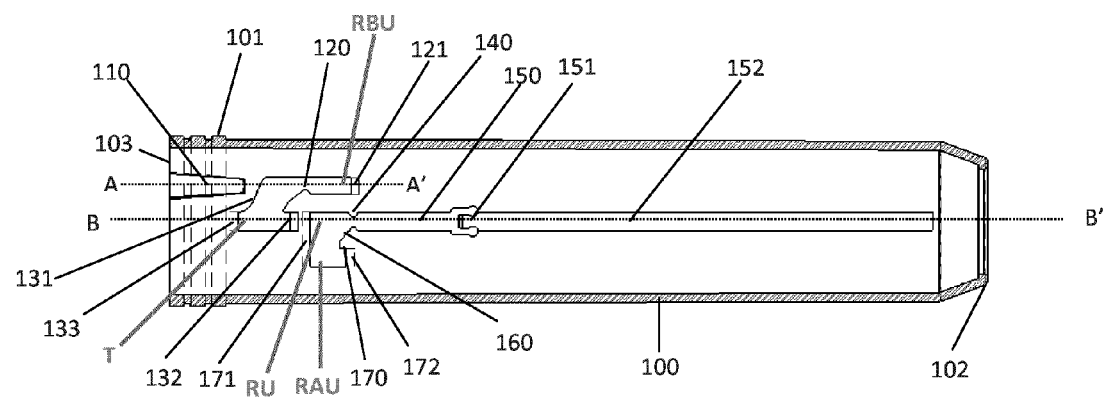
FIG. 3 is a cross-sectional view of a sheath according to the invention, showing transition and locking means.
Figure 4:
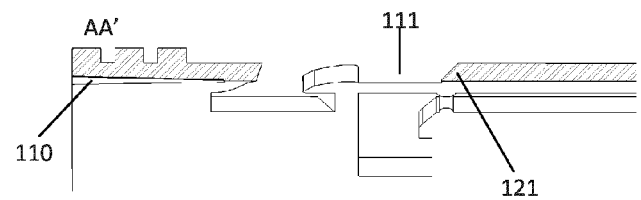
FIG. 4 is a partial cross-sectional view of the sheath according to the invention showing primary transition means.
Figure 5:
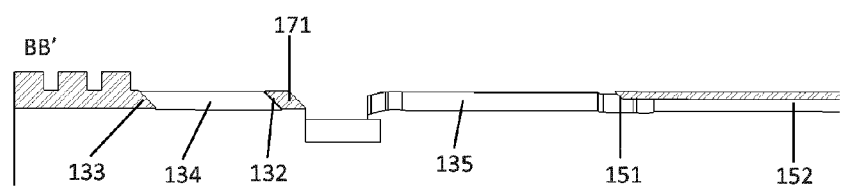
FIG. 5 is a partial cross-sectional view of the sheath according to the invention showing secondary transition means and guiding means.

A primary transition means comprises a groove 110 (in the preferred embodiment shown in FIG. 1, a second groove 110' is also provided) that is made by scooping out the interior surface of the sheath 100 to obtain the groove, opening only to the internal surface of said sheath 100, which ends at its distal end by an inclined plane directed to the interior of said sheath 100, leading thus the depth of said groove to a null value (FIG. 4). Said primary transition means 110 comprises a hole 111 which opens both to the internal and external surfaces 104 and 105 of said sheath 100, located further to the inclined plane toward the distal end 102 of said sheath 100. The width of the groove of said primary transition means 110, as illustrated in FIG. 3, has a width increasing gradually as one approaches the proximal end 103 of the sheath 100. The function of this feature is to facilitate the insertion of male means 201 of the hub 200 in the sheath 100.

A primary locking means 120 comprises a lug, located between two holes opening to both internal and external surfaces 104 and 105 of the sheath 100. This lug, in complement to the walls of the sheath 100 which prevent male means 201 to go further toward the distal end 102 of the sheath 100, maintains said male means 201 in the RBU position.

A secondary transition means 130 comprises two guiding means:

a translation/rotation guiding means 131, and a longitudinal translation guiding means 132.

A translation/rotation guiding means 131 consists in a hole (represented as 111 and 134) and a wall of the sheath 100, being designed as to present a curved and smooth shape so that when longitudinally moving male means 201 from the RBU position toward the proximal end 103 of the sheath 100, said male means 201 slightly rotate to move to the T position (FIG. 3).

A longitudinal translation guiding means 132 is made by an inclined plane directed toward the interior of the sheath 100, located next to the T position regarding the X axis. Said longitudinal guiding means 132 comprises at its proximal and distal ends holes 134 and 135 opening both to the external and internal surface of the sheath 100, as described in FIG. 5. By longitudinally moving male means 201 toward the distal end 102 of the sheath 100 from the T position, said male means 201 are pushed inside the sheath 100 by the guiding means 132 and emerge in the RU position just next to said guiding means 132. A guiding means 132 is advantageously a one-way transition means.

The slope of the inclined planes directed toward the interior of the sheath 100 ranges preferably from 10% to 30%, more preferably of about 20%, to promote smooth transition from one position to another.

The secondary blocking means 140 is formed of a lug 140, configured so that male means 201 may be maintained in longitudinal distal abutment in the position RU. Male means 201 are further radially maintained in the position RU by on the one hand a wall of the sheath 100, and on the other hand tertiary transition means 160. The secondary blocking means 140 is designed so that the passage forth from the position RU to the position E and back from the position E to the position RU requires a force high enough to push the lug apart.

A guiding means is provided that comprises a longitudinal groove 150 which opens to both internal and external surface 104 and 105 of the sheath 100 in a first part, and to only the internal surface 104 of said sheath 100 in a second part 152. Between these two parts, the guiding means comprises an inclined plane 151 directed toward the interior of the sheath 100, to allow a smooth transition from the first part of the groove to the second part 152. The second part 152 of the groove ends up substantially at the distal end 102 of the sheath 100, approximately at the beginning of the conical distal end of said sheath 100. Male means 201 may be stopped by the end of the guide means, and/or optionally by the return of the sheath wall inside the sheath 100, at its distal end 102.

The groove of the guiding means 150 preferably opens to the internal surface 104 and not to the external surface 105 of the sheath 100. This feature provides reinforcement for the guiding of male means 201 with the matter which covers the bottom of the grooves and which forms the grooves. However, it is possible to make the grooves open to both internal and external surfaces 104 and 105 of the sheath 100, or to make the grooves open to both internal and external surfaces 104 and 105 in a first part and open to only the internal surface 104 in a second part.

The tertiary transition means is formed of a lug 160 having an inclined plane so that male means 201 may move from the position RU to the position RAU, via a force high enough to put said lug apart. Once in the position RAU, the lug 160, by means of the final locking means in the form of a surface 170 of the lug 160, prevents said male means 201 to step back. Thus, the lug, via its surfaces at 160 and 170, is both a transition and locking means.

In the position RAU, male means 201 are further immobilized via the walls of the sheath 100. The hub 200 is therefore definitely locked in the RAU position, and cannot go forward or backward with regard to the sheath 100.

Injection System

The present invention further relates to an injection system, comprising a sheath 100 and a hub 200, inserted within said sheath 100.

Figure 6:
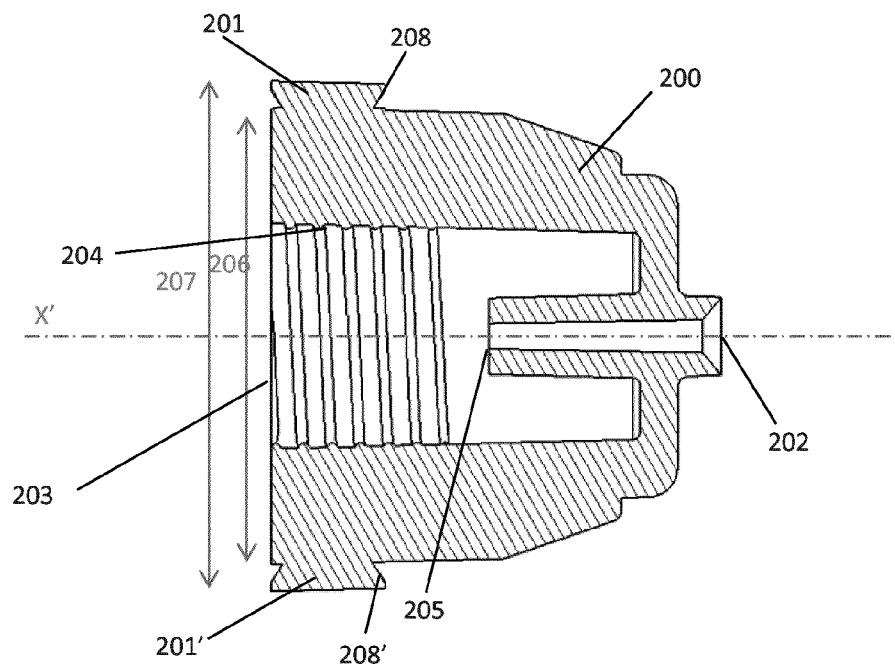
FIG. 6 is a cross-sectional view of a hub according to the invention.

The hub 200 has an overall shape of a cylinder having a longitudinal axis X', as described in FIG. 6. The hub 200 is open at its proximal end 203 and is closed at its distal end 202 on the cannula 210 or on a cylindrical cavity for the reception of the cannula 210. The hub 200 comprises a reception means 204 at its proximal end 203, designed to receive the distal end of a syringe 300, which is the end farthest to the thumb area 311.

In one embodiment, the reception means 204 is a thread allowing a clipping or a screwing of the distal end of a syringe 300. This thread may be sectioned by two longitudinal slots, for ensuring a clipping by pulling away the two threaded parts forming each a jaw, during the positioning of the hub 200 on the syringe distal end.

In one embodiment, wherein the hub comprises a cannula 210, said cannula 210 protrudes both distal end 202 and the bottom 205 of the reception means 204. When the distal end of a syringe 300 is engaged in the reception means 204, the cannula 210 is thus in fluid communication with the content of said syringe 300 via its proximal end 211. In other words, the content of the syringe 300 may be flowed through the cannula 210 from the proximal end 211. The content of said syringe 300 may be for example a pharmaceutical composition, which may be contained within a cartridge 400 or the barrel of said syringe 300, depending on the syringe type. In another embodiment the cannula may comprise two separate parts (i.e. two cannulae) one protruding outside of the distal end of the hub and one protruding outside of the proximal end of the hub; said two cannulae being fluidly connected inside the hub.

In an embodiment, the hub is used to move between the various position implemented in the sheath, to hold the cannula and, optionally, to fluidly connected the cannulae; however the hub is not design to protect the user from the cannula.

The hub 200 has an external diameter 206 slightly inferior to the diameter of the internal surface 104 of the sheath 100.

In one embodiment, the hub 200 further comprises at least one, or two, three, four, five or six; preferably two male means 201 diametrically opposite regarding the axis X'. In one embodiment, the hub 200 further comprises at least one male means 201. In a preferred embodiment, the hub 200 further comprises at least two male means 201 diametrically opposite regarding the axis X'. In another embodiment, the hub 200 further comprises at least three male means 201 regularly spaced on the circumference of the hub 200. In another embodiment, the hub 200 further comprises at least four male means 201 regularly spaced on the circumference of the hub 200. In another embodiment, the hub 200 further comprises at least five male means 201 regularly spaced on the circumference of the hub 200. In another embodiment, the hub 200 further comprises at least six male means 201 regularly spaced on the circumference of the hub 200. At these male means, the diameter 207 is greater than the diameter of the internal surface 104 of the sheath 100, and preferably substantially identical (permitting a variation of 10%, 5%, or 1% for example), or slightly inferior, to the diameter of the external surface 105 of the sheath 100.

In an embodiment, the hub 200 does not contain a U-shaped channel or groove around the male means 201.

The hub 200 is intended to be introduced at the proximal end 103 of the sheath 100, so that the axes X and X' line up. Male means 201 are thus advantageously adapted to be inserted in female means of the sheath 100.

In one embodiment, male means 201 of the hub 200 are outwards projections such as bosses.

In one embodiment, male means 201 of the hub 200 are bosses.

In an embodiment, the injection system of the invention comprises a sheath 100 and a hub 200 inserted in said sheath 100, wherein male means 201 are in a RBU position.

In an embodiment, the injection system of the invention is delivered to the user with the male means 201 in a RBU position.

In an embodiment, the sheath 100 of the present invention is not self-deploying.

The I position is thus used during the manufacturing and assembly of the injection system of the invention.

Syringe

Figure 8:
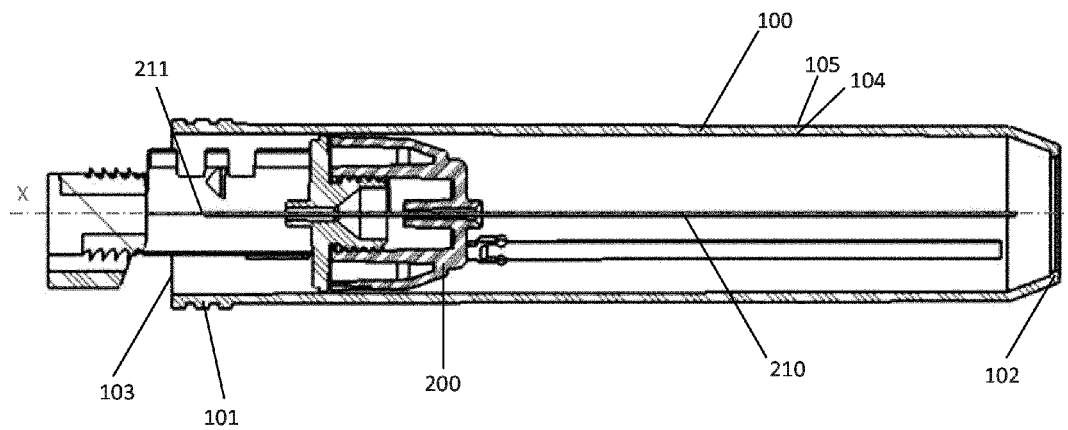
FIG. 8 is a cross-sectional view showing a hub, a sheath and a portion of a syringe according to the invention, said syringe being screwed into the hub and said hub being inserted into the sheath.

This invention also relates to a syringe 300, preferably to a dental syringe for the injection of a pharmaceutical composition, for instance, of a local anesthetic agent, comprised within a cartridge 400 or the barrel of said syringe 300; said syringe 300 being equipped with a sheath 100 protecting an injection needle or cannula 210 arranged on a hub 200, or being equipped with an injection system according to the invention comprising a sheath 100, a hub 200 and a cannula 210 (FIG. 8).

In one embodiment, no other piece than the sheath 100 is intended to protect the cannula 210: in other words, the sheath 100 is the only safety part for the protection of the cannula 210.

In one embodiment, no spring is involved in the protection of the cannula 210, for example in an automatic passage from an extended position to a retracted position, preventing thus a hazardous release of said spring.

The hub 200 is intended to be positioned at the distal end of the syringe 300, and is aimed at ensuring the entry of the proximal end 211 of the cannula 210 within the cartridge 400 or barrel containing the pharmaceutical composition. In one embodiment, the hub 200 is screwed on the distal end of the syringe 300.

In another embodiment, the hub 200 and the syringe 300 are integrally jointly formed.

In one embodiment, the syringe 300 is a standard syringe.

In another preferred embodiment, the syringe 300 is designed to hold a cartridge 400.

In the embodiment, wherein the syringe 300 is designed to hold a cartridge 400, said syringe is equipped with at least one means to hold a cartridge 400. Preferably, the syringe 300 is equipped in a first section of a first means to hold a cartridge 400, and is equipped in a second section of a second means to hold said cartridge 400, said means being complementary to safely hold said cartridge 400.

Figure 9:
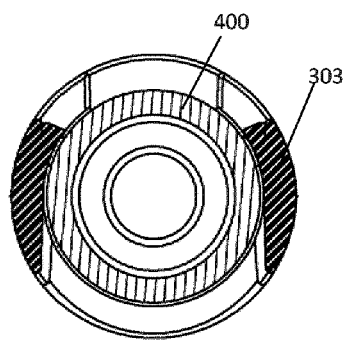
FIG. 9 is a cross-sectional view showing a cartridge held by a self demolding clip inside a syringe according to the invention.

In one embodiment, first means to hold the cartridge 400 are self demolding clips 303, presenting a protrusion to hold said cartridge 400, said protrusion being flexible enough to allow the insertion of said cartridge 400 (FIG. 9).

Figure 10:
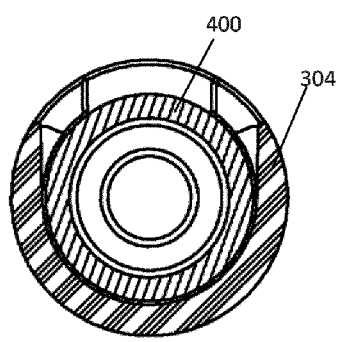
FIG. 10 is a cross-sectional view showing a cartridge held by the back of a syringe according to the invention.

In one embodiment, the second means to hold the cartridge 400 is the bottom of the syringe 304, as described in FIG. 10.

By these means, the cartridge 400 is totally immobilized in radial direction once inserted into the self demolding clip, avoiding thus to fall out of the syringe 300.

The cartridge 400 is immobilized in axial direction via a blocking means 305. An axial immobilization is of great importance for the present invention, since active aspiration is therefore allowed by suction of the rear piston 401 of the cartridge 400. This is particularly useful in dental care, during anesthesia for instance. The dentist loads a cartridge containing the anesthetic agent in a syringe and inserts then the needle tip into the gum. If the needle tip is inserted into a blood vessel, a depression will immediately aspirate blood into the cartridge. The dentist, in order to avoid an injection of anesthetics into a blood vessel, will be averted by the change of the anesthetic color.

Instead of axially fixing the rear of the cartridge 400 as it is the case in common syringes, the cartridge 400 is advantageously maintained at its neck 402, so that the length of the cartridge 400 does no longer play a role in the aspiration process. The syringe of the invention is therefore adaptable on cartridges having different lengths.

Figure 11:
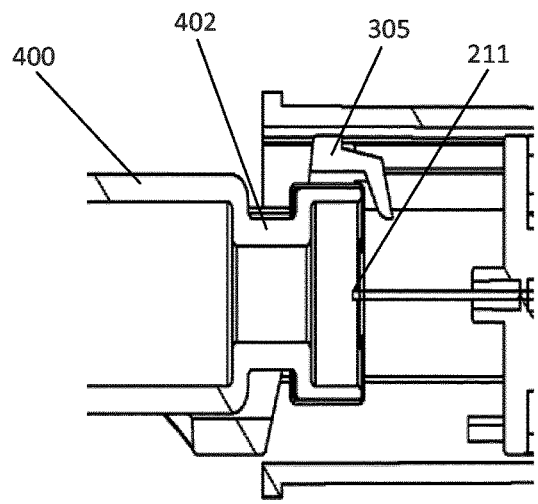
FIG. 11 is a cross-sectional view showing a cartridge being inserted into a syringe according to the invention.

In one embodiment, the blocking means 305 is a clip, as shown in FIG. 11. Preferably, the blocking means 305 also immobilizes the cartridge 400 radially.

Figure 12:
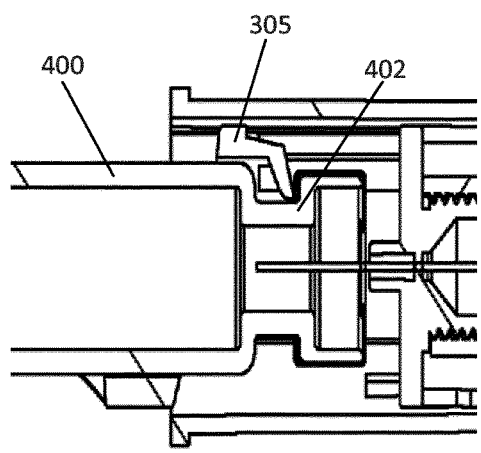
FIG. 12 is a cross-sectional view showing a cartridge inserted into a syringe according to the invention.

The blocking means 305 is advantageously flexible, allowing the cartridge insertion. When the cartridge 400 is pushed into the end position, the cartridge head will push the blocking means 305 up (FIG. 11). Once the cartridge 400 is in place, the blocking means 305 drops back and holds the cartridge 400 at its neck 402, immobilizing thus said cartridge 400 for active aspiration (FIG. 12).

An advantage of using such a flexible blocking means is the provision of passive aspiration. The blocking means 305 may indeed be slightly pushed upward during each pressure on the plunger 310 of the syringe 300, and will then come back to its initial position creating a depression in the cannula 210. Preferably, the blocking means 305 allows the cartridge 400 to travel between 1 and 5 mm, more preferably between 2 and 4 mm, to assure passive aspiration.

During active aspiration, the plunger 310 of the syringe 300 may be provided with a fixation connecting said plunger to the rear piston 401 of the cartridge 400 to assure the pulling of said rear piston of said cartridge. Such a fixation is for example a barb or a harpoon, or any other means adaptable to the rear piston of a cartridge.

In a preferred embodiment, the syringe plunger 310 is able to create a depression in the cartridge 400, aspirating thus the cartridge rear piston 401 and causing a depression in the cannula 210.

Figure 13:
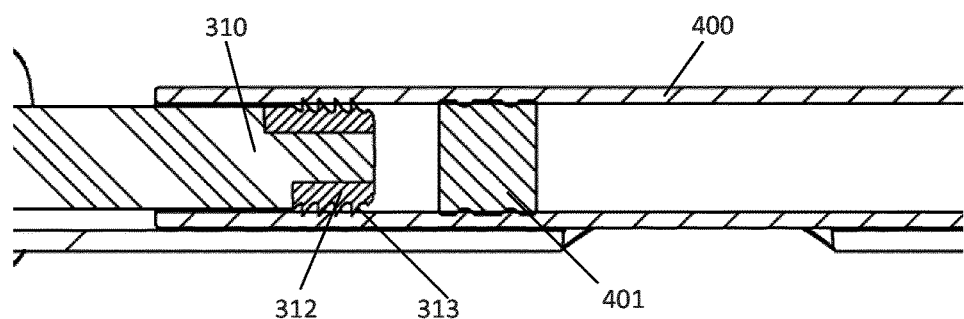
FIG. 13 is a cross-sectional view showing a plunger equipped with a vacuum plunger seal according to the invention, inserted into a cartridge.

In this embodiment, the syringe plunger 310 is preferably provided with a plunger seal 312, as described in FIG. 13.

The plunger 312 seal creates a depression between the syringe plunger 310 and the rear piston 401 of the cartridge 400 when the user pulls on the syringe piston, which results in an aspiration in the cartridge 400.

The plunger seal 312 comprises advantageously lips which may bend backwards (i.e. towards the proximal part of the plunger), allowing an easier introduction into the cartridge 400 without destroying the seal area. When pushing the plunger 310 in the cartridge 400, the air between the cartridge rear piston 401 and the vacuum plunger seal 312 expels since the lips can fold back, allowing the air to leave the space.

Whereas the fixation of a plunger to the rear piston of a cartridge has generally to be adapted in function of the cartridge type, an advantage of using such a plunger seal 312 is the adaptability on several types of cartridge.

In one embodiment, the vacuum plunger seal 312 is overmolded on the plunger 310.

Chirurgical instruments are manipulated with latex gloves. During the operation the gloves get wet and the friction forces of the gloves rubbers are reduced.

Figure 14:
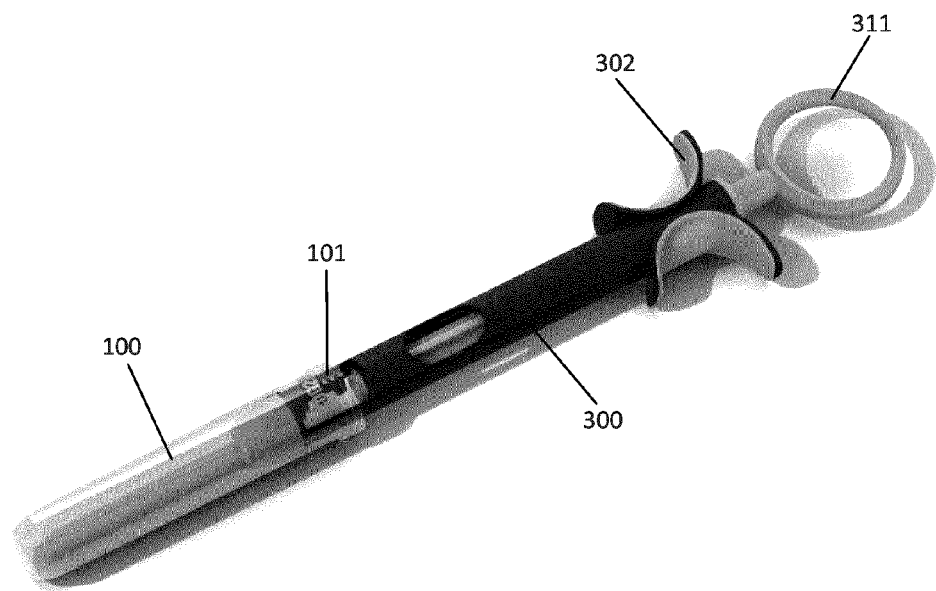
FIG. 14 is a perspective front view of a cartridge syringe equipped with a sheath according to the invention.

When using a plastic part with wet gloves the finger slipping could introduce injuries to the patient. In order to increase the grip, soft overmolding may be installed in the thumb area 311, and in the grip area 302 of the syringe 300, as depicted FIG. 14. A surface treatment like erosion graining VDI 20 to 30 or surface grindings, nobs or ribs may also be used to increase the surface friction.

Material for these grips may be for example SEBS, TPU, TPE, preferably SEBS (Kraiburg Thermoplast W, Soloplast TH, etc.).

In combination with the gripping means 101 of the sheath 100, the syringe of the invention provides a comfortable and safe use.

In one embodiment, the syringe of the invention is a disposable syringe, and allows preferably only a single use.

In this embodiment, the syringe 300 may have the particularity to be conveniently broken after use, in order to separate the sticking part from the non-sticking part. In one embodiment, the sticking part comprises the cannula 210 covered by the sheath 100, the sheath 100, the hub 200 and a optionally the distal end of the syringe 300 which is engaged in the reception means 204 of the hub 200, and the non-sticking part comprises substantially the totality of the syringe 300 which may comprise a cartridge 400.

This has the advantage to reduce the volume of sticking waste having a high risk of contamination, which has to be withdrawn in special containers whose decontamination and destruction are cost intensive. Another advantage is to avoid the congestion of the low volume waste boxes used by medical personal operating in reduced space.

Further to make the end of life of the syringe comfortable, another advantage of such a breakable syringe is the increased difficulty to uncover the cannula 210 after use. The cannula 210 may not be accidentally pushed out of the sheath 100 and become exposed, rendering a needlestick injury even less likely to happen.

Figure 15:
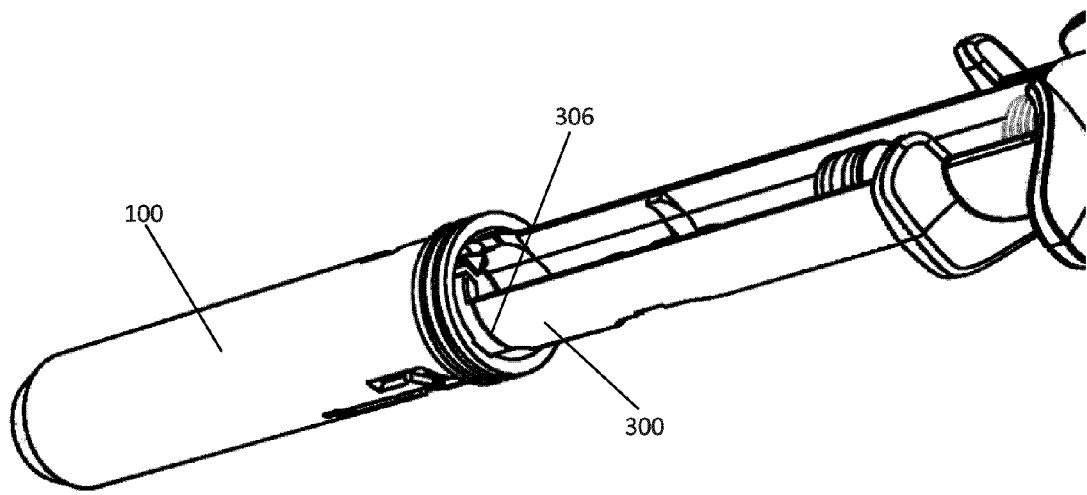
FIG. 15 is a perspective view of a disposable syringe according to the invention, comprising a circumferential groove for a defined break.
Figure 16:
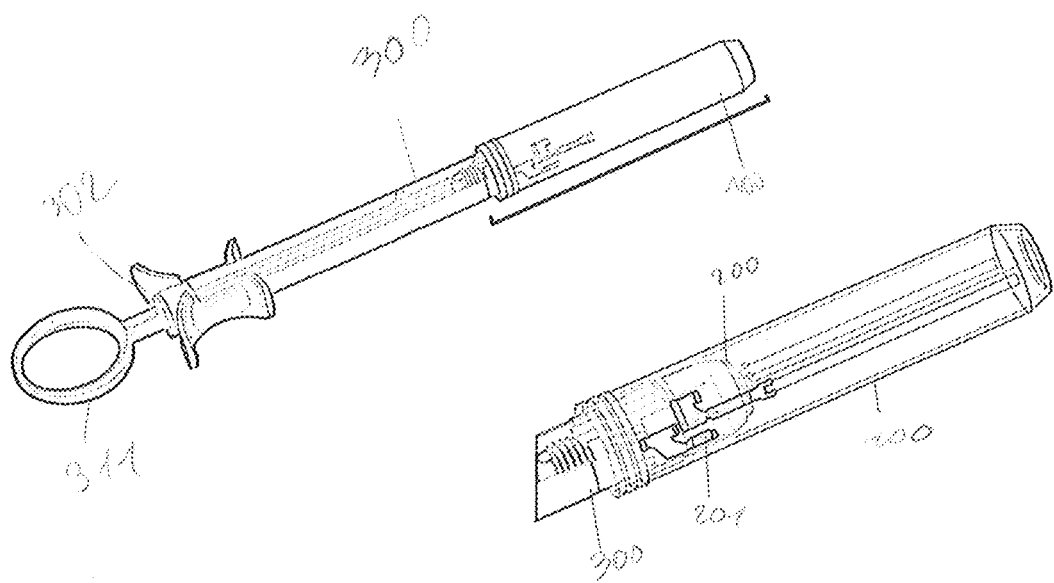
FIG. 16 shows a view and detail of a cartridge syringe equipped with the inventive sheath in a configuration before use.
Figure 17:
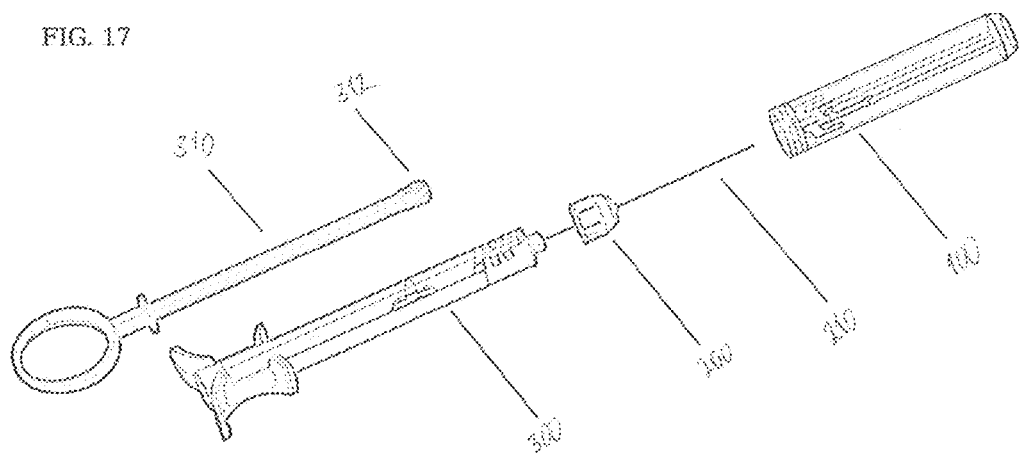
FIG. 17 shows an exploded view of the cartridge syringe equipped with the inventive sheath.
Figure 18:
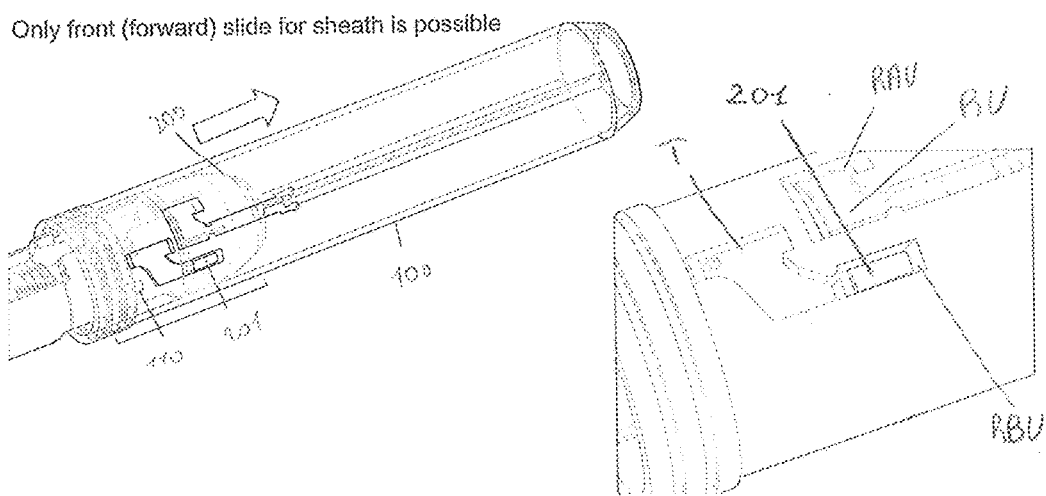
FIG. 18 shows a view and detail of the inventive sheath in position on the cartridge syringe in a beginning RBU position.
Figure 19:
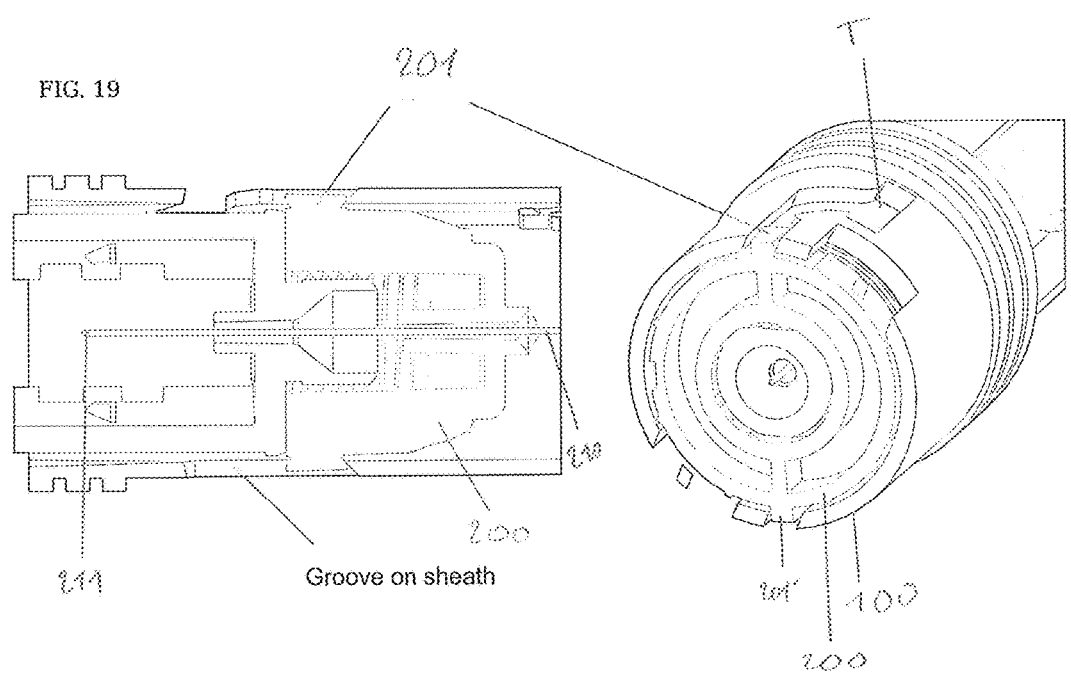
FIG. 19 illustrates two cross-sections of the sheath fitted on the cartridge syringe.
Figure 20:
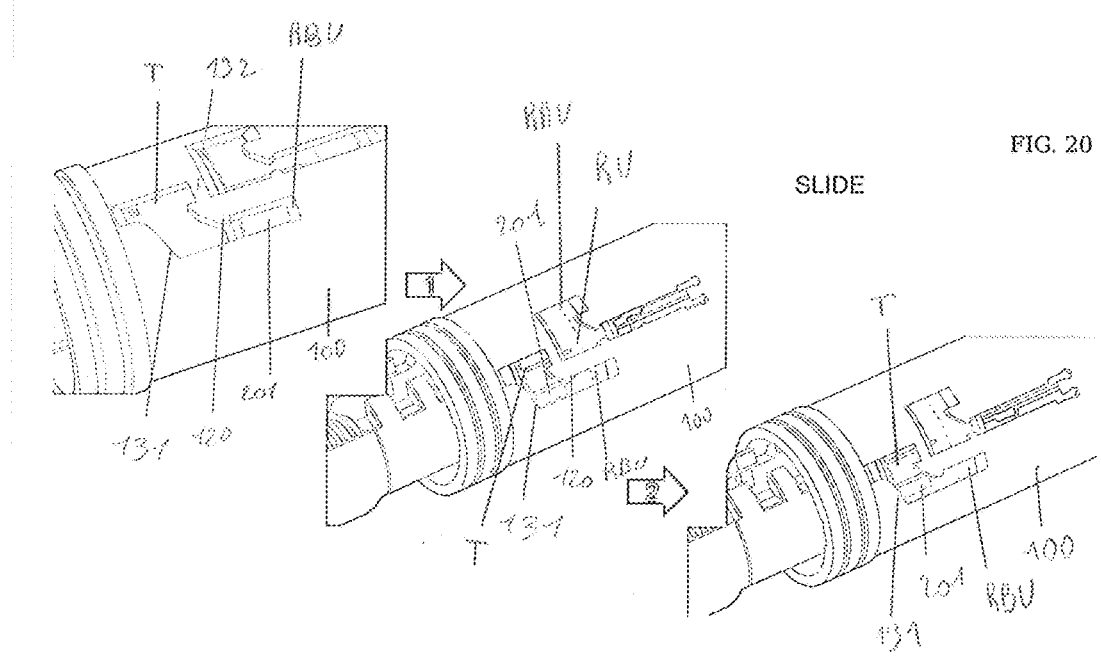
FIG. 20 schematically illustrates how the sheath slides with respect to the cartridge syringe to unlock the syringe from the RBU position to the T position.
Figure 21:
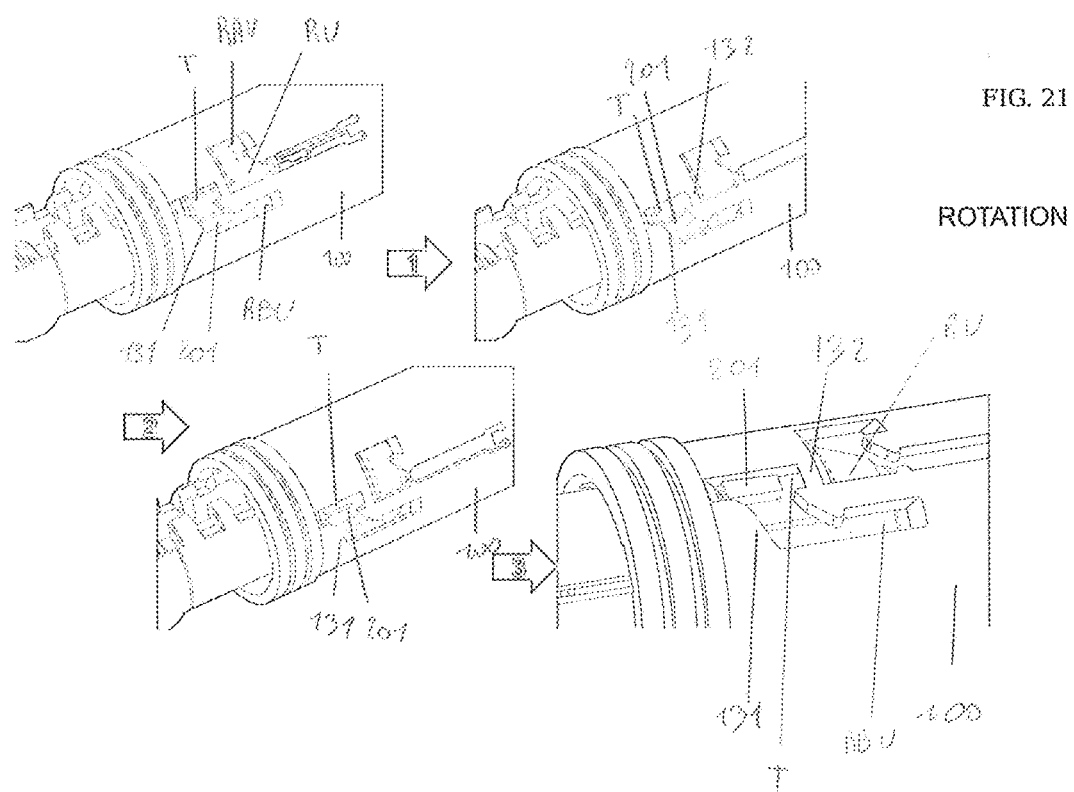
FIG. 21 schematically illustrates rotational movement of the sheath to unlock and prepare the syringe from the RBU position to the T position.
Figure 22:
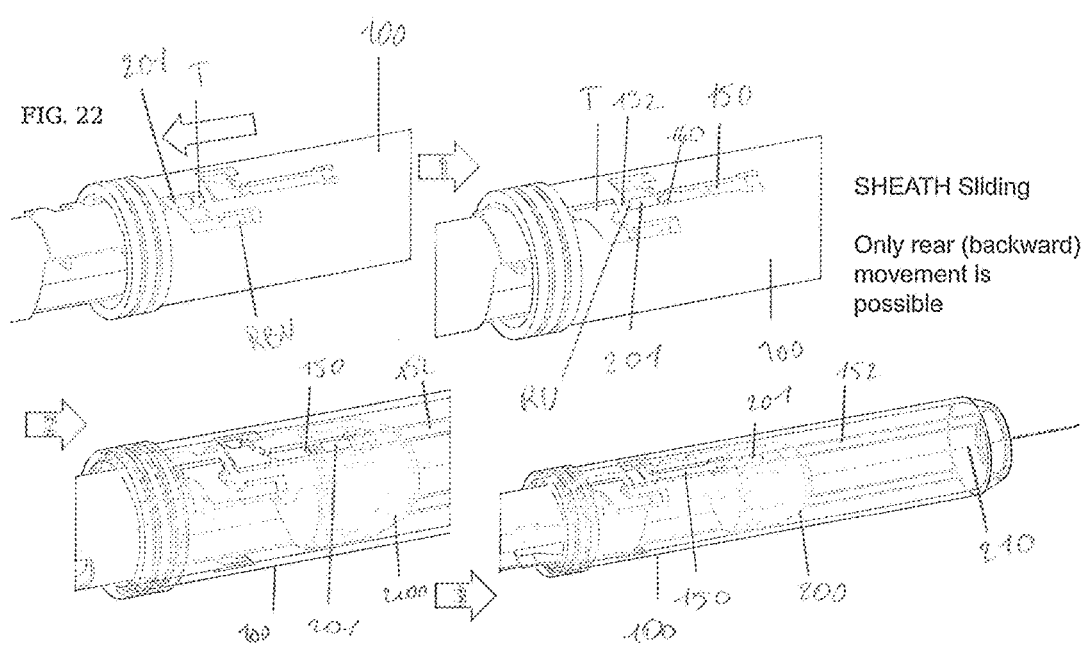
FIG. 22 schematically illustrates further sliding movement of the sheath to activate the cartridge syringe from the T position to the RU position and from the RU position to the E position.
Figure 23:
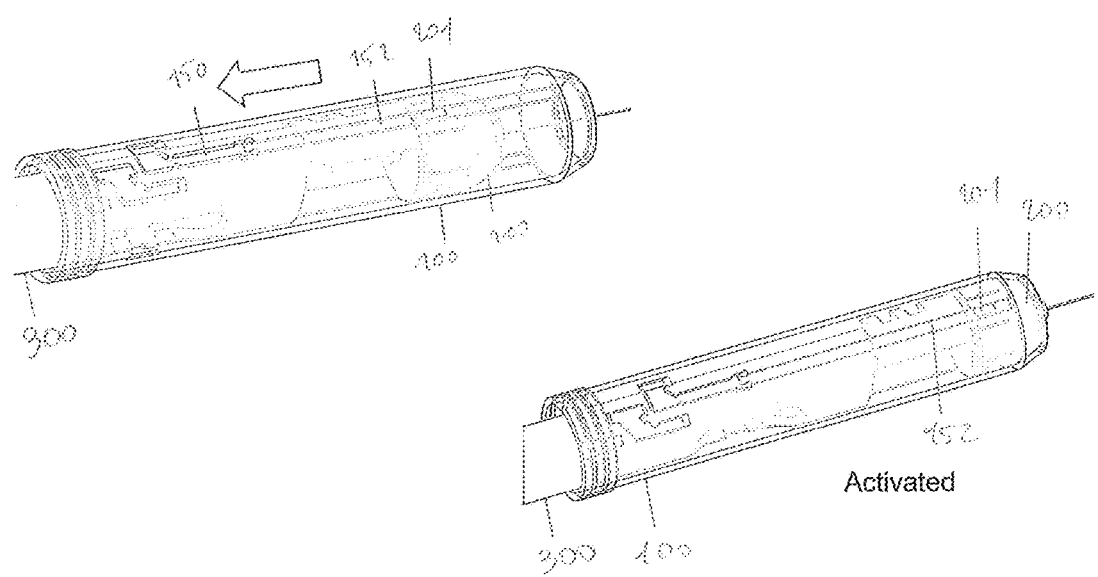
FIG. 23 schematically illustrates activation of the cartridge syringe by way of a sliding of the sheath with respect to the syringe in the E position.
Figure 24:
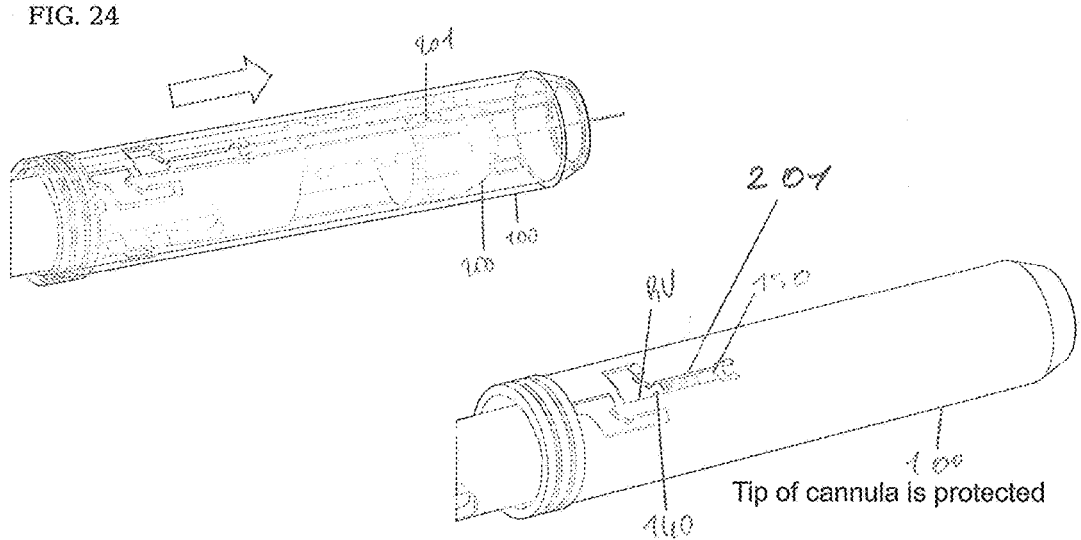
FIG. 24 schematically illustrates the removal of the tip of cannula.
Figure 25:
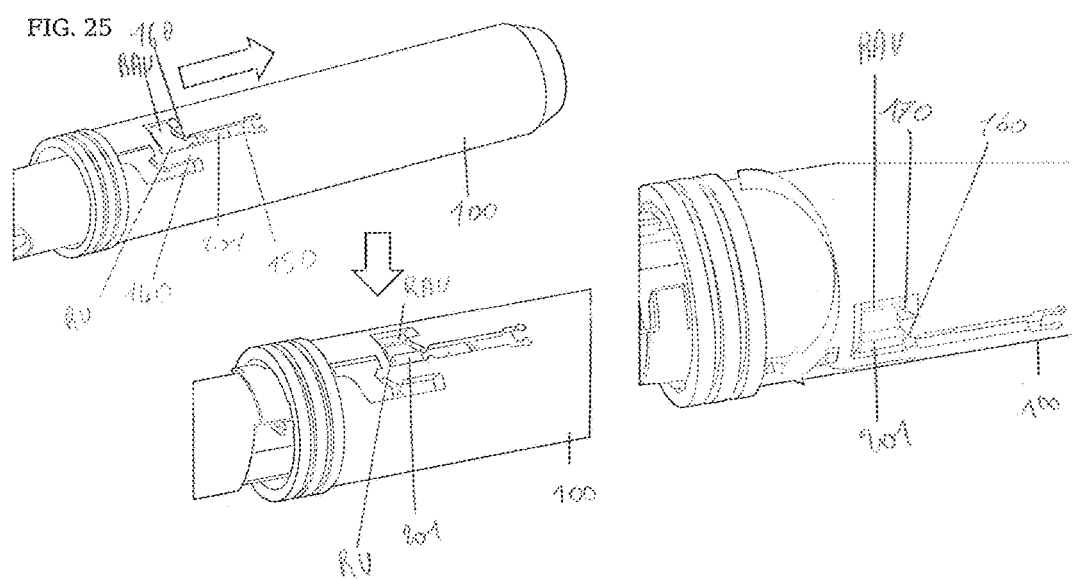
FIG. 25 schematically illustrates sheath movement relative to the cannula and the hub from the E position to the RU position.
Figure 26:
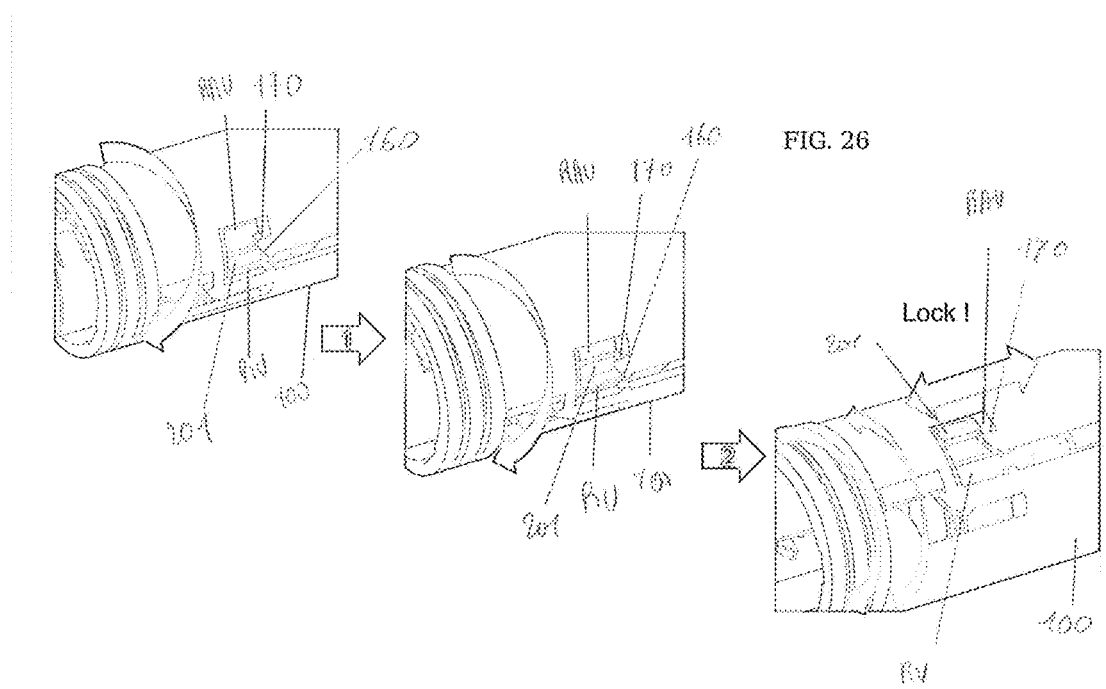
FIG. 26 schematically illustrates sheath movement being rotated from the RU position into the lock position RAU for deactivating the device.
Figure 27:
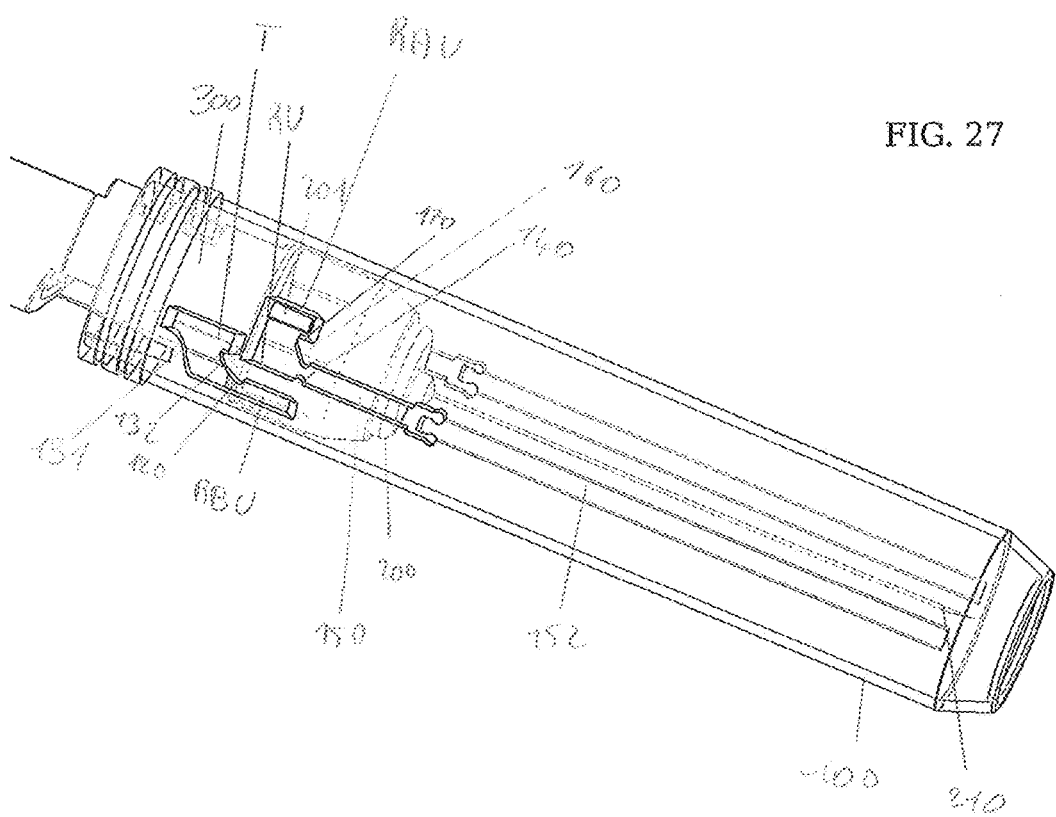
FIG. 27 shows a view of the inventive sheath in position on the cartridge syringe in an end position RAU wherein the sheath is in a final locked position.

A means for an easy and defined breakage is for example a precut 306, made of a series of perforations, or one or more circumferential grooves, located substantially at the distal end of the syringe 300, for example in the last 3 cm, 2 cm, 1 cm or 5 mm of said syringe 300. Preferably, a means for an easy and defined breakage is a circumferential groove, as depicted in FIG. 15.

In the embodiment wherein the syringe 300 is disposable, and wherein the final locked position for the hub 200 in the sheath 100 is reached via an unscrewing movement, the invention provides a really convenient end of life by an unscrewing movement followed by a break.

This invention also relates to a syringe 300 as described above, said syringe 300 being preferably equipped with a clip 305 as described above, and said syringe 300 being equipped with no sheath 100 and no injection system according to the invention.

In one embodiment, the syringe 300 of the present invention comprises a cartridge 400 which is immobilized in radial direction via demolding clips 303 and the back of the syringe 304.

In one embodiment, the syringe 300 of the present invention comprises a plunger 310 equipped with a plunger seal 312 comprising lips, wherein said lips may bend backwards for an easier introduction into the cartridge 400, said plunger seal 312 being optionally overmolded on the plunger 310.

In one embodiment, the syringe 300 of the present invention comprises soft overmoldings installed in the thumb area 311 and in the grip area 302 of said syringe 300.

In one embodiment, the syringe 300 of the present invention comprises a precut 306 located substantially at the distal end of the syringe 300, made of a series of perforations or one or more circumferential grooves, preferably one circumferential groove.

In another embodiment, the syringe 300 of the present invention comprises the following features:
the cartridge 400 is immobilized in radial direction via demolding clips 303 and the back of the syringe 304; and
the plunger 310 of said syringe 300 is equipped with a plunger seal 312 comprising lips, wherein said lips may bend backwards for an easier introduction into the cartridge 400, said plunger seal 312 being optionally overmolded on the plunger 310.

In one embodiment, the syringe 300 of the present invention comprises the following features:
the cartridge 400 is immobilized in radial direction via demolding clips 303 and the back of the syringe 304; and
said syringe 300 comprises soft overmoldings installed in the thumb area 311 and in the grip area 302 of said syringe 300.

In one embodiment, the syringe 300 of the present invention comprises the following features:
the cartridge 400 is immobilized in radial direction via demolding clips 303 and the back of the syringe 304; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
the plunger 310 of said syringe 300 is equipped with a plunger seal 312 comprising lips, wherein said lips may bend backwards for an easier introduction into the cartridge 400, said plunger seal 312 being optionally overmolded on the plunger 310; and
said syringe 300 comprises soft overmoldings installed in the thumb area 311 and in the grip area 302 of said syringe 300.

In one embodiment, the syringe 300 of the present invention comprises the following features:
the plunger 310 of said syringe 300 is equipped with a plunger seal 312 comprising lips, wherein said lips may bend backwards for an easier introduction into the cartridge 400, said plunger seal 312 being optionally overmolded on the plunger 310; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
said syringe 300 comprises soft overmoldings installed in the thumb area 311 and in the grip area 302 of said syringe 300; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
the cartridge 400 is immobilized in radial direction via demolding clips 303 and the back of the syringe 304;
the plunger 310 of said syringe 300 is equipped with a plunger seal 312 comprising lips, wherein said lips may bend backwards for an easier introduction into the cartridge 400, said plunger seal 312 being optionally overmolded on the plunger 310; and
said syringe 300 comprises soft overmoldings installed in the thumb area 311 and in the grip area 302 of said syringe 300.

In one embodiment, the syringe 300 of the present invention comprises the following features:
the cartridge 400 is immobilized in radial direction via demolding clips 303 and the back of the syringe 304;
the plunger 310 of said syringe 300 is equipped with a plunger seal 312 comprising lips, wherein said lips may bend backwards for an easier introduction into the cartridge 400, said plunger seal 312 being optionally overmolded on the plunger 310; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
the cartridge 400 is immobilized in radial direction via demolding clips 303 and the back of the syringe 304;
said syringe 300 comprises soft overmoldings installed in the thumb area 311 and in the grip area 302 of said syringe 300; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
the plunger 310 of said syringe 300 is equipped with a plunger seal 312 comprising lips, wherein said lips may bend backwards for an easier introduction into the cartridge 400, said plunger seal 312 being optionally overmolded on the plunger 310;
said syringe 300 comprises soft overmoldings installed in the thumb area 311 and in the grip area 302 of said syringe 300; and
said syringe 300 has a precut 306 located substantially at the distal end of the syringe 300, made of a series of perforations or one or more circumferential grooves, preferably one circumferential groove.

In one embodiment, the syringe 300 of the present invention comprises the following features:
the cartridge 400 is immobilized in radial direction via demolding clips 303 and the back of the syringe 304;
the plunger 310 of said syringe 300 is equipped with a plunger seal 312 comprising lips, wherein said lips may bend backwards for an easier introduction into the cartridge 400, said plunger seal 312 being optionally overmolded on the plunger 310;
said syringe 300 comprises soft overmoldings installed in the thumb area 311 and in the grip area 302 of said syringe 300; and
said syringe 300 has a precut 306 located substantially at the distal end of the syringe 300, made of a series of perforations or one or more circumferential grooves, preferably one circumferential groove.

This invention further relates to a manufacturing device, preferably a mould or an assembly machine, for manufacturing a sheath 100, a hub 200, and/or a syringe 300 according to the invention.

The invention claimed is:

1. A protective sheath (100) for a cannula (210) arranged on a hub (200) fittable upon a syringe, said sheath (100) comprising:
a hollow cylindrical body extending along a longitudinal axis, the cylindrical body provided with cavities in a thickness of the cylindrical body forming female features configured to cooperate with a male element (201) of the hub (200) for guiding a movement of the sheath, wherein,
said female features are configured to guide the cylindrical body into any one of a retracted before use (RBU) position, a retracted during use (RU) position, and a retracted after use (RAU) position where, in the RAU position, an entire length of the cannula (210) is received inside the cylindrical body,
said female features are further configured to guide the cylindrical body into an ejection (E) position where at least part of the cannula (210) protrudes outwardly from the cylindrical body, and
each of the three RBU, RU, and RAU positions are transversally aligned.

2. The protective sheath (100) according to claim 1, wherein said female features include:
a primary transition structure (110) that receive the male element (201) of the hub (200) for guiding said male element (201) to the RBU position;
a primary locking structure (120) that temporarily locks said male element (201) in the RBU position;
a secondary transition structure (130) that guides said male element (201) from the RBU to the RU position;

a secondary locking structure (140) that temporarily locks said male element (201) in the RU position;
a guiding structure (150), that guides said male element (201) forth from the RU position to the E position and back from the E position to the RU position;
a tertiary transition structure (160) that guides said male element (201) from the RU position to the RAU position; and/or
a final locking structure (170) that permanently locks said male element (201) in the RAU position.

3. The protective sheath (100) according to claim 2, wherein said tertiary transition structure (160) include a rotational guiding structure.

4. The protective sheath (100) according to claim 2, wherein said secondary transition structure (130) includes a translation/rotation guiding structure (131) that guides the male element (201) from the RBU position to a transitory position T, and a longitudinal guiding structure (132) that guides said male element (201) from the T position to the RU position.

5. The protective sheath (100) according to claim 4, wherein said longitudinal guiding structure (132) is a one-way transition structure comprising an anti-return structure.

6. The protective sheath (100) according to claim 1, further comprising:
anti-slipping means, which includes at least one of:
inclined planes (121, 133, 171, 172) and/or at least one rib (106), and
at least one rib (107) that prevents dismounting of the hub (200) from said sheath (100).

7. The protective sheath (100) according to claim 1, wherein the distal end (102) of said sheath (100) is any of conical or beveled.

8. The protective sheath (100) according to claim 1, further comprising:
a gripping structure (101) constituting ribs covered by a grinding or an erosion grain, located on an external surface (105) of said sheath (100).

9. The protective sheath (100) according to claim 1, wherein each of the RBU, RU, and RAU positions are transversally aligned such that each point has a same coordinate plus or minus 3 mm.

10. An injection system, comprising:
a protective sheath (100) for a cannula (210), the protective sheath (100) comprising a hollow cylindrical body extending along a longitudinal axis, the protective sheath (100) arranged on a hub (200) which can be fitted onto a syringe, said sheath (100) comprising female features configured to cooperate with a male element (201) of the hub (200) for guiding thereof, wherein:
said female features are configured to guide the cylindrical body into any one of a retracted before use (RBU) position, and a retracted after use (RAU) position where, in the RAU position, an entire length of the cannula (210) is received inside the cylindrical body,
said female features are further configured to guide the cylindrical body into an ejection (E) position where at least part of the cannula (210) protrudes outwardly from said the cylindrical body, and
each of the three RBU, RU, and RAU positions are transversally aligned; and
a hub (200), inserted within said sheath (100).

11. The injection system according to claim 10 wherein said female features include:

a primary transition structure (110) that receives the male element (201) of the hub (200) and guides said male element (201) to the RBU position;
a primary locking structure (120) that temporarily locks said male element (201) in the RBU position;
a secondary transition structure (130) that guides said male element (201) from the RBU to the RU position;
a secondary locking structure (140) that temporarily locks said male element (201) in the RU position;
a guiding structure (150), that guides said male element (201) forth from the RU position to the E position and back from the E position to the RU position;
a tertiary transition structure (160) that guides said male element (201) from the RU position to the RAU position; and/or
a final locking structure (170) that permanently locks said male element (201) in the RAU position.

12. The injection according to claim 10, wherein the hub (200) comprises:
said male element (201), adapted to cooperate with said female features of said sheath (100) wherein the hub (200) is inserted.

13. The injection system according to claim 12, wherein the hub (200) further comprises:
a cannula (210), protruding at both ends of the hub (200).

14. The injection system according to claim 10, wherein each of the RBU, RU, and RAU positions are transversally aligned such that each point has a same coordinate plus or minus 3 mm.

15. A syringe system, comprising:
a syringe; and
a protective sheath (100) for a cannula (210), the protective sheath (100) comprised of a hollow cylindrical body extending along a longitudinal axis, the protective sheath (100) arranged on a hub (200) which is fittable onto the syringe, said sheath (100) comprising female features that cooperates with a male element (201) of the hub (200) for guiding thereof, wherein:
said female features are configured to guide the cylindrical body into any one of a retracted before use (RBU) position, a retracted during use (RU) position, and a retracted after use (RAU) position where, in the RAU position an entire length of the cannula (210) is received inside the cylindrical body,
said female features are further configured to guide the cylindrical body into an ejection (E) position where at least part of the cannula (210) protrudes outwardly from of the cylindrical body, and
each of the three RBU, RU, and RAU positions are transversally aligned.

16. The syringe system according to claim 15, further comprising:
a hub (200) inserted within the sheath (100).

17. The syringe system according to claim 15, wherein the system is configured to hold a cartridge (400) such that the cartridge (400) is immobilized in an axial direction at a neck (402) of said cartridge (400) via a flexible clip (305).

18. The syringe system according to claim 15, wherein the syringe is a disposable syringe having a precut (306) located substantially at a distal end of said syringe system, made of a series of perforations or one or more circumferential grooves.

19. The syringe system according to claim 15,
wherein the cartridge (400) is immobilized in radial direction, and
wherein the plunger (310) of said syringe is equipped with a plunger seal (312) comprising lips (313).

20. The syringe system according to claim 15, further comprising:
  soft overmoldings located in a thumb area (311) and in a grip area (302) of said syringe system.

21. The injection system according to claim 15, wherein each of the RBU, RU, and RAU positions are transversally aligned such that each point has a same coordinate plus or minus 3 mm.

* * * * *